(12) United States Patent
Hafner et al.

(10) Patent No.: US 6,900,328 B2
(45) Date of Patent: May 31, 2005

(54) PROCESS FOR THE SYNTHESIS OF AMINE ETHERS FROM SECONDARY AMINO OXIDES

(75) Inventors: Andreas Hafner, Gelterkinden (CH); Hans Jürg Kirner, Pratteln (CH); Franz Schwarzenbach, Frenkendorf (CH); Paul Adriaan Van Der Schaaf, Allschwil (CH); Peter Nesvadba, Marly (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 84 days.

(21) Appl. No.: 10/296,107

(22) PCT Filed: May 17, 2001

(86) PCT No.: PCT/EP01/05668

§ 371 (c)(1),
(2), (4) Date: Nov. 22, 2002

(87) PCT Pub. No.: WO01/92228

PCT Pub. Date: Dec. 6, 2001

(65) Prior Publication Data

US 2003/0171461 A1 Sep. 11, 2003

(30) Foreign Application Priority Data

May 26, 2000 (EP) ............................................. 00810461

(51) Int. Cl.$^7$ ............................................ C07D 211/54
(52) U.S. Cl. ....................... 546/216; 540/451; 540/485; 544/106; 544/359
(58) Field of Search .................... 546/216; 540/451, 540/485; 544/106, 359

(56) References Cited

U.S. PATENT DOCUMENTS 4,921,962 A * 5/1990 Galbo et al. ................. 546/184
6,117,995 A * 9/2000 Zedda et al. ................. 544/207

FOREIGN PATENT DOCUMENTS

| DE | 19907945 | | 8/1999 | |
|---|---|---|---|---|
| EP | 0569334 | | 11/1993 | |
| WO | WO 99/46261 | * | 9/1999 | ......... C07D/405/12 |

OTHER PUBLICATIONS

Connolly et al, Tetrahedron Letter, vol. 37, No. 28, 1996, pp 4919–4922.*
T. J. Connelly et al., Tetrahedron Letters, vol. 37, No. 28, (1996), pp. 4919–4922.

* cited by examiner

Primary Examiner—Zinna Northington Davis
(74) Attorney, Agent, or Firm—Tyler A. Stevenson

(57) ABSTRACT

An amine ether of formula (A) wherein a is 1 or 2; and when a is 1, E is E'; when a is 2, E is L; E' is $C_1$–$C_{36}$ alkyl; $C_3$–$C_{18}$ alkenyl; $C_2$–$C_{18}$ alkinyl; $C_5$–$C_{18}$ cycloalkyl; $C_5$–$C_{18}$ cycloalkenyl; a radical of a saturated or unsaturated aliphatic bicyclic or tricyclic hydrocarbon of 7 to 12 carbon atoms; $C_2$–$C_7$alkyl or $C_3$–$C_7$alkenyl substituted by halogen; $C_7$–$C_{15}$aralkyl or $C_7$–$C_{15}$ aralkyl substituted by $C_1$–$C_4$ alkyl or phenyl; or E' is a radical of formula (VII) as explained in claim 1; T' is tertiary $C_4$–$C_{18}$alkyl or phenyl, each of which are unsubstituted or substituted by halogen, OH, $COOR_{21}$ or C(O)—$R_{22}$; or T' is $C_5$–$C_{12}$cycloalkyl; $C_5$–$C_{12}$cacloalkyl which is interrupted by at least one O or —$NR_{18}$—; a polycyclic alkyl radical having 7-18 carbon atoms, or the same radical which is interrupted by at least one O or —$NR_{18}$—; or T' is —$C(G_1)(G_2)$—T"; or $C_1$–$C_{18}$alkyl or $C_5$–$C_{12}$cycloalkyl substituted by F(I)T" is hydrogen, halogen, $NO_2$, cyano, or is a monovalent organic radical comprising 1-50 carbon atoms; or T" and T' together form a divalent organic linking group completing, together with the hindered amine nitrogen atom and the quaternary carbon atom substituted by $G_1$ and $G_2$, an optionally substituted five- or six-membered ring structure; and all other residues are as defined in claim 1, are obtained in good yield from the corresponding N-oxyl hindered amine precursor by reaction with a hydrocarbon $E_1$—H or H—L—H in the presence of an organic hydroperoxide and a catalytic amount of copper or a copper compound. The products of present process find utility as polymerization regulators and/or light stabilizers for organic material (A)

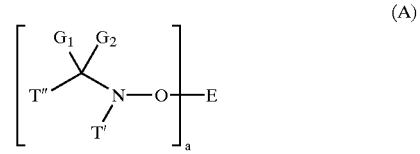

12 Claims, No Drawings

PROCESS FOR THE SYNTHESIS OF AMINE ETHERS FROM SECONDARY AMINO OXIDES

The instant invention pertains to a process for preparing amine ethers, e.g. N-hydrocarbyloxy substituted hindered amine compounds, by the reaction of the corresponding N-oxyl intermediate with a hydrocarbon in presence of an organic hydroperoxide and a copper catalyst, and some novel compounds obtainable by this process. The compounds made by the instant process are particularly effective in the stabilization of polymer compositions against harmful effects of light, oxygen and/or heat; they are also useful as initiators or regulators for radical polymerization processes which provide homopolymers, random copolymers, block copolymers, multiblock copolymers, graft copolymers and the like, at enhanced rates of polymerization and enhanced monomer to polymer conversions.

4-Hydroxy-1-oxyl-2,2,6,6-tetramethylpiperidine and 4-oxo-1-oxyl-2,2,6,6-tetramethylpiperidine are described as scavengers for some carbon centered radicals (S. Nigam et al., J. Chem. Soc., Trans. Faraday Soc., 1976, (72), 2324 and by K.-D. Asmus et al., Int. J. Radiat. Biol., 1976, (29), 211).

D. H. R. Barton et al., Tetrahedron, 1996, (52), 10301 describe the formation of some N-alkoxy-2,2,6,6-tetramethylpiperidine derivatives in the reaction of hydrocarbons with iron(II) and iron(III) species, hydrogen peroxide and various coadditives in the presence of N-oxyl-2,2,6,6-tetramethylpiperidine (TEMPO).

U.S. Pat. No 5,374,729 describes a process for the preparation of N-methoxy derivatives of hindered amines from the reaction of the corresponding N-oxyl compound with methyl radicals produced from dimethyl sulfoxide by decomposing aqueous hydrogen peroxide in presence of a metal salt or by thermal decomposition of di-tert.butyl peroxide.

U.S. Pat. No. 4,921,962 describes a process for the formation of N-hydrocarbyloxy derivatives of sterically hindered amines in which a hindered amine or N-oxyl substituted hindered amine is reacted with a hydrocarbon solvent in the presence of a hydroperoxide and a molybdenum catalyst.

It has now been found that N-hydrocarbyloxy substituted sterically hindered amines can most suitably be prepared from the N-oxyl intermediate and a hydrocarbon in presence of an organic hydroperoxide and a copper catalyst. The process of the invention uses only catalytic quantities of copper and does not require high temperatures.

Thus, present invention pertains to a process for the preparation of an amine ether of the formula A

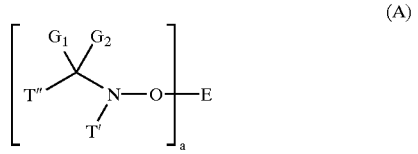

(A)

wherein
a is 1 or 2;
when a is 1, E is E'
when a is 2, E is L;
E' is $C_1$–$C_{36}$ alkyl; $C_3$–$C_{18}$ alkenyl; $C_2$–$C_{18}$ alkinyl; $C_5$–$C_{18}$ cycloalkyl; $C_5$–$C_{18}$ cycloalkenyl; a radical of a saturated or unsaturated aliphatic bicyclic or tricyclic hydrocarbon of 7 to 12 carbon atoms; $C_2$–$C_7$alkyl or $C_3$–$C_7$alkenyl substituted by halogen, $C_1$–$C_8$alkoxy or phenoxy; $C_4$–$C_{12}$heterocycloalkyl; $C_4$–$C_{12}$heterocycloalkenyl; $C_7$–$C_5$ aralkyl or $C_4$–$C_{12}$heteroaralkyl, each of which is unsubstituted or substituted by $C_1$–$C_4$ alkyl or phenyl; or E' is a radical of formula (VII) or (VIII)

(VII)

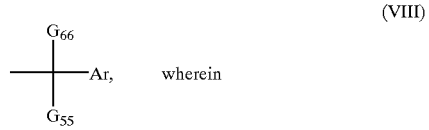

(VIII)

wherein

Ar is $C_6$–$C_{10}$aryl or $C_5$–$C_9$heteroaryl;
X is phenyl, naphthyl or biphenyl, which are substituted by 1, 2, 3 or 4 D and optionally further substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino;
D is a group

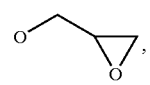

a group C(O)—$G_{13}$ or a group C(O)—$G_9$—C(O)—$G_{13}$;
$G_1$ and $G_2$, independently of each other, are hydrogen, halogen, $NO_2$, cyano, —$CONR_5R_6$, —($R_9$)$COOR_4$, —C(O)—$R_7$, —$OR_8$, —$SR_8$, —$NHR_8$, —$N(R_{18})_{21}$ carbamoyl, di($C_1$–$C_{18}$alkyl)carbamoyl, —C(=$NR_5$)(NHR_6), $C_1$–$C_{18}$alkyl; $C_3$–$C_{18}$alkenyl; $C_3$–$C_{18}$alkinyl, $C_7$–$C_9$phenylalkyl, $C_3$–$C_{12}$cycloalkyl or $C_2$–$C_{12}$heterocycloalkyl; $C_1$–$C_{18}$alkyl or $C_3$–$C_{18}$alkenyl or $C_3$–$C_{18}$alkinyl or $C_7$–$C_9$phenylalkyl, $C_3$–$C_{12}$cycloalkyl or $C_2$–$C_{12}$heterocycloalkyl substituted by OH, halogen, $NO_2$, amino, cyano, carboxy, $COOR_{21}$, C(O)—$R_{22}$, $C_1$–$C_4$alkoxy, $C_1$–$C_4$alkylthio, $C_1$–$C_4$alkylamino or di($C_1$–$C_4$alkyl)amino or a group —O—C(O)—$R_7$; $C_2$–$C_{18}$alkyl which is interrupted by at least one O atom and/or $NR_5$ group; or are $C_6$–$C_{10}$aryl; or phenyl or naphthyl which are substituted by $C_1$–$C_4$alkyl, $C_1$–$C_4$alkoxy, $C_1$–$C_4$alkylthio, halogen, cyano, hydroxy, carboxy, $COOR_{21}$, C(O)—$R_{22}$, $C_1$–$C_4$alkylamino or di($C_1$–$C_4$alkyl)amino; or $G_1$ and $G_2$ together with the linking carbon atom form a $C_3$–$C_{12}$cycloalkyl radical;
$G_5$ and $G_6$ are independently of each other H or $CH_3$;
$G_9$ is $C_1$–$C_{12}$alkylene or a direct bond;
$G_{13}$ is $C_1$–$C_{18}$alkyl;
$G_{14}$ is $C_1$–$C_{18}$alkyl, $C_5$–$C_{12}$cycloalkyl, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, or acyl radical of an aromatic acid containing 7 to 15 carbon atoms;
$G_{55}$ is H, $CH_3$ or phenyl;
$G_{66}$ is —CN or a group of the formula —$COOR_4$ or —$CONR_5R_6$ or —$CH_2$—O—$G_{14}$;
L is alkylene of 1 to 18 carbon atoms, cycloalkylene of 5 to 8 carbon atoms, cycloalkenylene of 5 to 8 carbon atoms, alkenylene of 3 to 18 carbon atoms, alkylene of 1 to 12 carbon atoms substituted by phenyl or by phenyl substituted by alkyl of 1 to 4 carbon atoms; or is alkylene of 4 to 18 carbon atoms interrupted by COO and/or phenylene;
T' is tertiary $C_4$–$C_{18}$alkyl or phenyl, each of which are unsubstituted or substituted by halogen, OH, $COOR_{21}$ or C(O)—R$_{22}$; or T' is C$_5$–C$_{12}$cycloalkyl; C$_5$–C$_{12}$cycloalkyl which is interrupted by at least one O or —NR$_{18}$—; a polycyclic alkyl radical having 7–18 carbon atoms, or the same radical which is interrupted by at least one O or —NR$_{18}$—; or T' is —C(G$_1$)(G$_2$)—T''; or C$_1$–C$_{18}$alkyl or C$_5$–C$_{12}$cycloalkyl substituted by

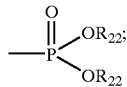

T'' is hydrogen, halogen, NO$_2$, cyano, or is a monovalent organic radical comprising 1–50 carbon atoms;

or T'' and T' together form a divalent organic linking group completing, together with the hindered amine nitrogen atom and the quaternary carbon atom substituted by G$_1$ and G$_2$, an optionally substituted five- or six-membered ring structure; and R$_4$ is hydrogen, C$_1$–C$_{18}$alkyl, phenyl, an alkali metal cation or a tetraalkylammonium cation;

R$_5$ and R$_6$ are hydrogen, C$_1$–C$_{18}$alkyl, C$_2$–C$_{18}$alkyl which is substituted by hydroxy or, taken together, form a C$_2$–C$_{12}$alkylene bridge or a C$_2$–C$_{12}$-alkylene bridge interrupted by O or/and NR$_{18}$;

R$_7$ is hydrogen, C$_1$–C$_{18}$alkyl or C$_6$–C$_{10}$aryl;

R$_8$ is hydrogen, C$_1$–C$_{18}$alkyl or C$_2$–C$_{18}$hydroxyalkyl;

R$_9$ is C$_1$–C$_{12}$alkylene or a direct bond;

R$_{18}$ is C$_1$–C$_{18}$alkyl or phenyl, which are unsubstituted or substituted by halogen, OH, COOR$_{21}$ or C(O)—R$_{22}$;

R$_{21}$ is hydrogen, a alkali metal atom or C$_1$–C$_{18}$alkyl; and R$_{22}$ is C$_1$–C$_{18}$alkyl;

which process comprises reacting a N-oxyl amine of formula B

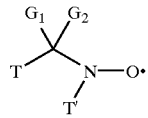 (B)

with a compound of formula IV or V

 (IV)

 (V)

in the presence of an organic hydroperoxide and a catalytic amount of copper or a copper compound.

Preferred is a process for the synthesis of an- amine ether of formula A

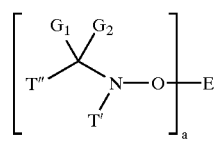 (A)

wherein a is 1 or 2;

when a is 1, E is E' when a is 2, E is L;

E' is C$_1$–C$_{36}$ alkyl; C$_3$–C$_{18}$ alkenyl; C$_2$–C$_{18}$ alkinyl; C$_5$–C$_{18}$ cycloalkyl; C$_5$–C$_{18}$ cycloalkenyl; a radical of a saturated or unsaturated aliphatic bicyclic or tricyclic hydrocarbon of 7 to 12 carbon atoms; C$_2$–C$_7$alkyl or C$_3$–C$_7$alkenyl substituted by halogen; C$_7$–C$_{15}$ aralkyl or C$_7$–C$_{15}$ aralkyl substituted by C$_1$–C$_4$ alkyl or phenyl; or E' is a radical of formula (VII)

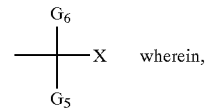 (VII)

X is phenyl, naphthyl or biphenyl, which are substituted by 1, 2, 3 or 4 D and optionally further substituted by NO$_2$, halogen, amino, hydroxy, cyano, carboxy, C$_1$–C$_4$alkoxy, C$_1$–C$_4$alkylthio, C$_1$–C$_4$alkylamino or di(C$_1$–C$_4$alkyl) amino;

D is a group

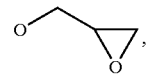

a group C(O)—G$_{13}$ or a group C(O)—G$_9$—C(O)—G$_{13}$;

G$_1$ and G$_2$, independently of each other, are hydrogen, halogen, NO$_2$, cyano, —CONR$_5$R$_6$—(R$_9$)COOR$_4$, —C(O)—R$_7$, —OR$_8$, —SR$_8$, —NHR$_8$, —N(R$_{18}$)$_2$, carbamoyl, di(C$_1$–C$_{18}$alkyl)carbamoyl, —C(=NR$_5$) (NHR$_6$), C$_1$–C$_{18}$alkyl; C$_3$–C$_{18}$alkenyl; C$_3$–C$_{18}$alkinyl, C$_7$–C$_9$phenylalkyl, C$_3$–C$_{12}$cycloalkyl or C$_2$–C$_{12}$heterocycloalkyl; C$_1$–C$_{18}$alkyl or C$_3$–C$_{18}$alkenyl or C$_3$–C$_{18}$alkinyl or C$_7$–C$_9$phenylalkyl, C$_3$–C$_{12}$cycloalkyl or C$_2$–C$_{12}$heterocycloalkyl substituted by OH, halogen, NO$_2$, amino, cyano, carboxy, COOR$_{21}$, C(O)—R$_{22}$, C$_1$–C$_4$alkoxy, C$_1$–C$_4$alkylthio, C$_1$–C$_4$alkylamino or di(C$_1$–C$_4$alkyl)amino or a group —O—C(O)—R$_7$; C$_2$–C$_{18}$alkyl which is interrupted by at least one O atom and/or NR$_5$ group; or are C$_6$–C$_{10}$aryl; or phenyl or naphthyl which are substituted by C$_1$–C$_4$alkyl, C$_1$–C$_4$alkoxy, C$_1$–C$_4$alkylthio, halogen, cyano, hydroxy, carboxy, COOR$_{21}$, C(O)—R$_{22}$, C$_1$–C$_4$alkylamino or di(C$_1$–C$_4$alkyl)amino; or G$_1$ and G$_2$ together with the linking carbon atom form a C$_3$–C$_{12}$cycloalkyl radical;

G$_5$ and G$_6$ are independently of each other H or CH$_3$;

G$_9$ is C$_1$–C$_{12}$alkylene or a direct bond;

G$_{13}$ is C$_1$–C$_{18}$alkyl;

L is alkylene of 1 to 18 carbon atoms, cycloalkylene of 5 to 8 carbon atoms, cycloalkenylene of 5 to 8 carbon atoms, alkenylene of 3 to 18 carbon atoms, alkylene of 1 to 12 carbon atoms substituted by phenyl or by phenyl substituted by alkyl of 1 to 4 carbon atoms;

T' is tertiary C$_4$–C$_{18}$alkyl or phenyl, each of which are unsubstituted or substituted by halogen, OH, COOR$_2$, or C(O)—R$_{22}$; or T' is C$_5$–C$_{12}$cycloalkyl; C$_5$–C$_{12}$cycloalkyl which is interrupted by at least one O or —NR$_{18}$—; a polycyclic alkyl radical having 7–18 carbon atoms, or the same radical which is interrupted by at least one O or —NR$_{18}$—; or T' is —C(G$_1$)(G$_2$)—T''; or C$_1$–C$_{18}$alkyl or C$_5$–C$_{12}$cycloalkyl substituted by

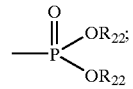

T'' is hydrogen, halogen, NO$_2$, cyano, or is a monovalent organic radical comprising 1–50 carbon atoms;

or T'' and T' together form a divalent organic linking group completing, together with the hindered amine nitrogen atom and the quaternary carbon atom substituted by $G_1$ and $G_2$, an optionally substituted five- or six-membered ring structure; and $R_4$ is hydrogen, $C_1$–$C_{18}$alkyl, phenyl, an alkali metal cation or a tetraalkylammonium cation;

$R_5$ and $R_6$ are hydrogen, $C_1$–$C_{18}$alkyl, $C_2$–$C_{18}$alkyl which is substituted by hydroxy or, taken together, form a $C_2$–$C_{12}$alkylene bridge or a $C_2$–$C_{12}$-alkylene bridge interrupted by O or/and $NR_{18}$;

$R_7$ is hydrogen, $C_1$–$C_{18}$alkyl or $C_6$–$C_{10}$aryl;

$R_8$ is hydrogen, $C_1$–$C_{18}$alkyl or $C_2$–$C_{18}$hydroxyalkyl;

$R_9$ is $C_1$–$C_{12}$alkylene or a direct bond;

$R_{18}$ is $C_1$–$C_{18}$alkyl or phenyl, which are unsubstituted or substituted by halogen, OH, $COOR_{21}$, or $C(O)$—$R_{22}$;

$R_{21}$ is hydrogen, a alkali metal atom or $C_1$–$C_{18}$alkyl; and $R_{22}$ is $C_1$–$C_{18}$alkyl;

which process comprises reacting a N-oxyl amine of formula B

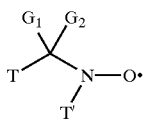
(B)

with a hydrocarbon of formula IV or V $E'$—H                       (IV)

H—L—H                    (V)

in the presence of an organic hydroperoxide and a catalytic amount of copper or a copper compound.

In particular, present invention pertains to a process for the synthesis of a hindered amine of formula I or II

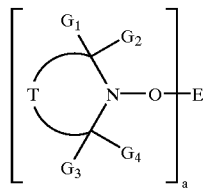
(I)

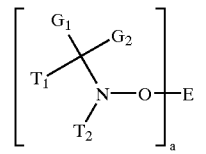
(II)

wherein $G_1$, $G_2$, $G_3$ and $G_4$ independently of each other are $C_1$–$C_{18}$alkyl; $C_3$–$C_{18}$alkenyl; $C_3$–$C_{18}$alkinyl; $C_1$–$C_{18}$alkyl or $C_3$–$C_{18}$alkenyl or $C_3$–$C_{18}$alkinyl substituted by OH, halogen or a group —O—C(O)—$R_5$; $C_2$–$C_{18}$alkyl which is interrupted by at least one O atom and/or $NR_5$ group; or are $C_3$–$C_{12}$cycloalkyl; or $C_6$–$C_{10}$aryl; or $G_1$ and $G_2$ and/or $G_3$ and $G_4$ together with the linking carbon atom form a $C_3$–$C_{12}$cycloalkyl radical;

a is 1 or 2;

when a is 1, E is E', wherein E' is $C_1$–$C_{36}$ alkyl; $C_2$–$C_{18}$alkenyl; $C_2$–$C_{18}$ alkinyl; $C_5$–$C_{18}$ cycloalkyl; $C_5$–$C_{18}$ cycloalkenyl; a radical of a saturated or unsaturated aliphatic bicyclic or tricyclic hydrocarbon of 7 to 12 carbon atoms; $C_2$–$C_7$alkyl or $C_3$–$C_7$alkenyl substituted by halogen; $C_7$–$C_{15}$ aralkyl or $C_7$–$C_{15}$ aralkyl substituted by $C_1$–$C_4$ alkyl or phenyl; or E' is a radical of formula (VII)

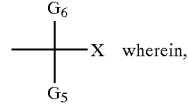
(VII)

X is phenyl, naphthyl or biphenyl, which are substituted by 1, 2, 3 or 4 D and optionally further substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl) amino;

D is a group

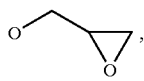

a group $C(O)$—$G_{13}$ or a group $C(O)$—$G_9$—$C(O)$—$G_{13}$;

when a is 2, E is L;

$G_5$ and $G_6$ are independently of each other H or $CH_3$;

$G_9$ is $C_1$–$C_{12}$alkylene or a direct bond;

$G_{13}$ is $C_1$–$C_{18}$alkyl;

L is alkylene of 1 to 18 carbon atoms, cycloalkylene of 5 to 8 carbon atoms, cycloalkenylene of 5 to 8 carbon atoms, alkenylene of 3 to 18 carbon atoms, alkylene of 1 to 12 carbon atoms substituted by phenyl or by phenyl substituted by alkyl of 1 to 4 carbon atoms;

T is a divalent organic radical required to complete formula I to form, together with the hindered amine nitrogen atom and the two quaternary carbon atoms substituted by $G_1$ and $G_2$ or $G_3$ and $G_4$, a five- or six-membered ring structure;

$T_1$ is hydrogen, halogen, $NO_2$, cyano, —($R_9$)$COOR_4$, —($R_9$)$C(O)$—$R_7$, —$OR_8$, unsubstituted $C_1$–$C_{18}$alkyl, $C_2$–$C_{18}$alkenyl, $C_2$–$C_{18}$alkynyl, $C_7$–$C_9$phenylalkyl, $C_3$–$C_{12}$cycloalkyl or $C_2$–$C_{12}$heterocycloalkyl; or $T_1$ is $C_1$–$C_{18}$alkyl, $C_2$–$C_{18}$alkenyl, $C_2$–$C_{18}$ alkynyl, $C_7$–$C_9$phenylalkyl, $C_3$–$C_{12}$cycloalkyl or $C_2$–$C_{12}$heterocycloalkyl, which is substituted by $NO_2$, halogen, hydroxy, cyano, carboxy, $C_1$–$C_6$alkanoyl, $C_1$–$C_{12}$alkoxy; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy; or $T_1$ is a residue —$CH_2$—O—$R_{10}$ or —$CH_2$—$NR_{18}$—$R_{10}$ or —$C(=CH_2)$—$R_{11}$ or —$C(=O)$—$R_{12}$;

$T_2$ is tertiary $C_4$–$C_{18}$alkyl or phenyl, which are unsubstituted or substituted by halogen, OH, $COOR_{21}$ or $C(O)$—$R_{22}$; or $T_2$ is $C_5$–$C_{12}$cycloalkyl; $C_5$–$C_{12}$cycloalkyl which is interrupted by at least one O; a polycyclic alkyl radical having 7–18 carbon atoms or the same radical which is interrupted by at least one O atom; or $T_2$ is —$C(G_1)(G_2)$—$T_1$; or

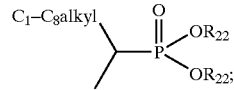

$R_4$ is hydrogen, $C_1$–$C_{18}$alkyl, phenyl, an alkali metal cation or a tetraalkylammonium cation;

$R_5$ is hydrogen, $C_1$–$C_{18}$alkyl or $C_6$–$C_{10}$aryl $R_7$ is hydrogen, $C_1$–$C_{18}$alkyl or phenyl;

$R_8$ is hydrogen, $C_1$–$C_{18}$alkyl or $C_2$–$C_{18}$hydroxyalkyl;

$R_9$ is $C_1$–$C_{12}$alkylene or a direct bond;

$R_{10}$ is hydrogen, formyl, $C_2$–$C_{18}$alkylcarbonyl, benzoyl, $C_1$–$C_{18}$alkyl, $C_5$–$C_{12}$cycloalkyl, $C_5$–$C_{12}$cycloalkyl interrupted by O or $NR_{18}$, or is benzyl or phenyl which are unsubstituted or substituted by halogen, OH, $COOR_{21}$ or $C(O)—R_{22}$;

$R_{11}$ is OH, $C_1$–$C_{18}$alkoxy, benzyloxy, O—C(O)—($C_1$–$C_{18}$)alkyl, $N(R_{18})_2$, or a group $C(O)R_{25}$;

$R_{12}$ is OH, O(alkali-metal), $C_1$–$C_{18}$alkoxy, benzyloxy, $N(R_{18})_2$;

$R_{18}$ is $C_1$–$C_{18}$alkyl or $C_2$–$C_{18}$hydroxyalkyl;

$R_{21}$ is hydrogen, a alkali metal atom or $C_1$–$C_{18}$alkyl; and $R_{22}$ is $C_1$–$C_{18}$alkyl;

$R_{25}$ is OH, $C_1$–$C_{18}$alkoxy, benzyloxy, $N(R_{18})_2$;

which process comprises reacting a N-oxyl hindered amine of formula III or IIIa

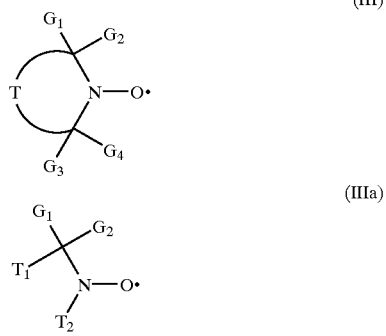

with a hydrocarbon of formula IV or V

E'—H  (IV)

H—L—H  (V)

in the presence of an organic hydroperoxide and a catalytic amount of copper or a copper compound.

In the context of the description of the present invention, the term alkyl comprises, for example, methyl, ethyl and the isomers of propyl, butyl, pentyl, hexyl, heptyl, octyl, nonyl, decyl, undecyl and dodecyl. Examples of aryl-substituted alkyl (aralkyl) are benzyl, α-methylbenzyl or cumyl. Examples of alkoxy are methoxy, ethoxy, propoxy, butoxy, octyloxy etc.. Examples of alkenyl are vinyl and especially allyl. Examples of alkylene including alkylidene are ethylene, n-propylene or 1,2-propylene.

Some examples of cycloalkyl are cyclobutyl, cyclopentyl, cyclohexyl, methylcyclopentyl, dimethylcyclopentyl and methylcyclohexyl.

Examples of aryl are phenyl and naphthyl. Examples of substituted aryl are methyl-, dimethyl-, trimethyl-, methoxy- or phenyl-substituted phenyl.

Some examples of an aliphatic carboxylic acid are acetic, propionic, butyric, stearic acid. An example of a cycloaliphatic carboxylic acid is cyclohexanoic acid. An example of an aromatic carboxylic acid is benzoic acid. An example of a phosphorus-containing acid is methylphosphonic acid. An example of an aliphatic dicarboxylic acid is malonyl, maleoyl or succinyl, or sebacic acid. An example of a residue of an aromatic dicarboxylic acid is phthaloyl.

A group heterocycloalkyl or heterocycloalkenyl embraces one or two heteroatoms, and a group heteroaryl from one to four heteroatoms, the heteroatoms being preferably selected from the group consisting of nitrogen, sulfur and oxygen. Some examples of heterocycloalkyl are tetrahydrofuryl, pyrrolidinyl, piperazinyl and tetrahydrothienyl. Some examples of heteroaryl are furyl, thienyl, pyrrolyl, pyridyl and pyrimidinyl. $C_2$–$C_{12}$heterocycloalkyl is typically oxirane, 1,4-dioxane, tetrahydrofuran, γ-butyrolactone, ε-caprolactam, oxirane, aziridine, diaziridine, pyrrole, pyrrolidine, thiophen, furan, pyrazole, imidazole, oxazole, oxazolidine, thiazole, pyran, thiopyran, piperidine or morpholine.

An example of a monovalent silyl radical is trimethylsilyl.

Polycyclic alkyl radicals which may also be interrupted by at least one oxygen or nitrogen atom are for example adamantane, cubane, twistane, norbomane, bycyclo[2.2.2]octane bycyclo[3.2.1]octane, hexamethylentetramine (urotropine) or a group

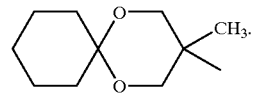

Acyl radicals of monocarboxylic acids are, within the definitions, a residue of the formula —CO—R", wherein R" may stand inter alia for an alkyl, alkenyl, cycloalkyl or aryl radical as defined. Preferred acyl radicals include acetyl, benzoyl, acryloyl, methacryloyl, propionyl, butyryl, valeroyl, hexanoyl, heptanoyl, octanoyl, nonanoyl, decanoyl, undecanoyl, dodecanoyl, pentadecanoyl, stearoyl. Polyacyl radicals of polyvalent acids are of the formula (—CO)$_n$—R", wherein n is the valency, e.g. 2, 3, 4, 5 or 6. Some preferred examples for such residues are given elsewhere.

In preferred products of the instant process, E' is selected from the group consisting of —$CH_2$-aryl,

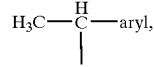

—$CH_2$—$CH_2$-aryl,

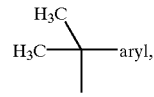

($C_5$–$C_6$cycloalkyl)$_2$CCN, ($C_1$–$C_{12}$alkyl)$_2$CCN, —$CH_2CH$=$CH_2$, ($C_1$–$C_{12}$)alkyl-$CR_{30}$—C(O)—($C_1$–$C_{12}$)alkyl, ($C_1$–$C_{12}$)alkyl-$CR_{30}$—C(O)—($C_6$–$C_{10}$)aryl, ($C_1$–$C_{12}$)alkyl-$CR_{30}$—C(O)—($C_1$–$C_{12}$)alkoxy, ($C_1$–$C_{12}$)alkyl-$CR_{30}$—C(O)-phenoxy, ($C_1$–$C_{12}$)alkyl-$CR_{30}$—C(O)—N-di($C_1$–$C_{12}$)alkyl, ($C_1$–$C_{12}$)alkyl-$CR_{30}$—CO—NH($C_1$–$C_{12}$)alkyl, ($C_1$–$C_{12}$)alkyl-$CR_{30}$—CO—$NH_2$, —$CH_2CH$=$CH$—$CH_3$, —$CH_2$—C($CH_3$)=$CH_2$, —$CH_2$—CH=CH-phenyl,

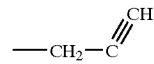

($C_1$–$C_{12}$)alkyl-$CR_{30}$—CN,

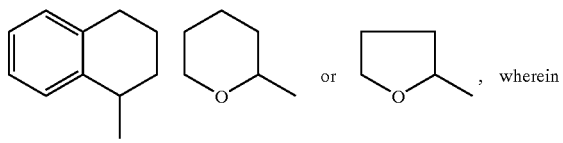

, wherein $R_{30}$ is hydrogen or $C_1$–$C_{12}$alkyl;

the aryl groups are phenyl or naphthyl, which are unsubstituted or substituted with $C_1$–$C_{12}$alkyl, halogen, $C_1$–$C_{12}$alkoxy, formyl, $C_2$–$C_{12}$alkylcarbonyl, glycidyloxy, OH, —COOH or —COO$C_1$–$C_{12}$alkyl.

More preferably E' is selected from the group consisting of —$CH_2$-phenyl, $CH_3CH$-phenyl, $(CH_3)_2C$-phenyl, $(C_5$–$C_6cycloalkyl)_2CCN$, $(CH_3)_2CCN$, —$CH_2CH=CH_2$, $CH_3CH$—$CH=CH_2$ $(C_1$–$C_8alkyl)CR_{30}$—$C(O)$-phenyl, $(C_1$–$C_8)alkyl$-$CR_{30}$—$C(O)$—$(C_1$–$C_8)alkoxy$, $(C_1$–$C_8)$ alkyl-$CR_{30}$—$C(O)$—$(C_1$–$C_8)alkyl$, $(C_1$–$C_8)alkyl$-$CR_{30}$—$C(O)$—$N$-di$(C_1$–$C_8)alkyl$, $(C_1$–$C_8)alkyl$-$CR_{30}$—$C(O)$—$NH(C_1$–$C_8)alkyl$, $(C_1$–$C_8)alkyl$-$CR_{30}$—$C(O)$—$NH_2$, $(C_1$–$C_{12})alkyl$-$CR_{30}$—$CN$, wherein $R_{30}$ is hydrogen or $(C_1$–$C_8)alkyl$.

$G_1$ and $G_2$ and/or $G_3$ and $G_4$ forming, together with the linking carbon atom, a $C_3$–$C_{12}cycloalkyl$ radical, preferably form a $C_5$–$C_{12}cycloalkyl$ radical, especially cyclopentylene, cyclohexylene or cycloheptylene.

$G_1$, $G_2$, $G_3$ and $G_4$ independently are preferably alkyl of 1 to 4 carbon atoms, or the adjacent radicals $G_1$ and $G_2$ and/or $G_3$ and $G_4$ together are pentamethylene. More preferably, $G_1$, $G_2$, $G_3$ and $G_4$ independently are methyl or ethyl or propyl, especially methyl or ethyl. In the products most preferred, $G_1$ and $G_3$ are each methyl while $G_2$ and $G_4$ independently are methyl, ethyl or propyl.

T usually is an organic linking group containing 2–500 carbon atoms and forming, together with the carbon atoms it is directly connected to and the nitrogen atom, a substituted, 5-, 6 or 7-membered cyclic ring structure; T is preferably a $C_2$–$C_{500}hydrocarbon$ optionally containing 1–200 hetero atoms selected from nitrogen, oxygen, phosphorus, sulfur, silicon and halogen, T therein can be part of a 6-membered cyclic ring structure. More preferably, T is an organic linking group of the formula

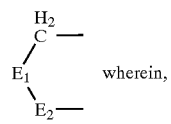

(VI)

wherein, $E_2$ is —CO— or —$(CH_2)_b$—, while b is 0, 1 or 2;

$E_1$ is a carbon atom carrying the two residues $R_{24}$ and $R_{25}$, or is >N—$R_{25}$, or is oxygen, and $R_{24}$ and $R_{25}$ are hydrogen or an organic residue, characterized in that the linking group T in total contains 2–500 carbon atoms and forms, together with the carbon atoms it is directly connected to it and the nitrogen atom, a substituted, 5-, 6 or 7-membered cyclic ring structure, or wherein $R_{24}$ and $R_{25}$ together are =O or wherein $R_{24}$ is hydrogen and $R_{25}$ is hydrogen or hydroxy. T is most preferably 2-hydroxy-1,3-propanediyl or 2-oxo-1,3-propanediyl.

Preferred products of the formula (I) are those wherein $G_1$, $G_2$, $G_3$ and $G_4$, independently of each other, are methyl, ethyl, phenyl or $COOR_4$;

E is a carbon centered radical formed from a $C_7$–$C_{11}phenylalkane$ or a $C_6$–$C_{10}pyridylalkane$; or $C_5$–$C_{12}cycloalkane$; or $C_5$–$C_{12}cycloalkene$; or an oxacyclohexane or oxycyclohexene; or $C_3$–$C_8alkene$; or $C_3$–$C_8alkene$ substituted by phenoxy; or a benzene which is substituted by $C_1$–$C_4alkyl$ and a further substituent selected from $C_1$–$C_4alkoxy$, glycidyl or glycidyloxy; or E is a radical of formula (VIII)

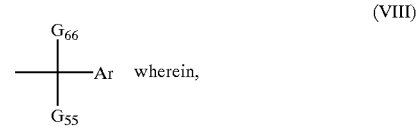

(VIII)

wherein,

Ar is $C_6$–$C_{10}aryl$ or $C_5$–$C_9heteroaryl$;

$G_{14}$ is $C_1$–$C_4alkyl$ or an acyl radical of an aliphatic carboxylic acid containing 2 to 4 carbon atoms or benzoyl;

$G_{55}$ is H, $CH_3$ or phenyl;

$G_{66}$ is —CN or a group of the formula —$COOR_4$ or —$CH_2$—$O$—$G_{14}$;

$R_4$ is hydrogen or $C_1$–$C_8alkyl$;

L is a carbon centered radical formed from propane, butane, pentane, 2,2-dimethyl-propane, xylene; and T is phenylene or an organic linking group of the formula

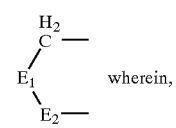

(VI)

wherein, $E_2$ is —CO— or —$(CH_2)_b$—, while b is 0, 1 or 2;

$E_1$ is a carbon atom carrying the two residues $R_{24}$ and $R_{25}$, or is >N—$R_{25}$, or is oxygen, and $R_{24}$ and $R_{25}$ are hydrogen or an organic residue, characterized in that the linking group T in total contains 2–500 carbon atoms and forms, together with the carbon atoms it is directly connected to it and the nitrogen atom, a substituted, 5-, 6 or 7-membered cyclic ring structure, or wherein $R_{24}$ and $R_{25}$ together are =O or wherein $R_{24}$ is hydrogen and $R_{25}$ is hydrogen or hydroxy;

or $E_1$ and $E_2$ together are 1,2-phenylene.

The product of formula A most preferably corresponds to one of the formulae

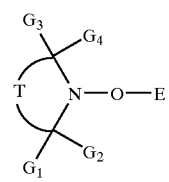

(X)

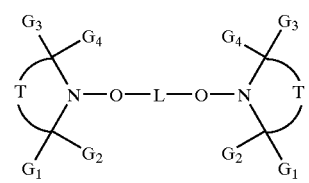

(XI)

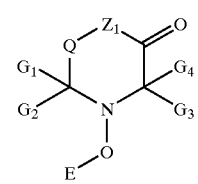

(XII)

-continued

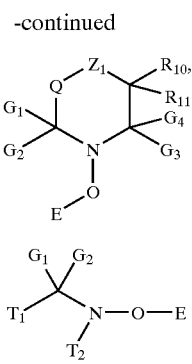

wherein
$G_1$, $G_2$, $G_3$ and $G_4$ independently of each other are $C_1$–$C_{18}$alkyl; $C_3$–$C_{18}$alkenyl; $C_3$–$C_{18}$alkinyl; $C_1$–$C_{18}$alkyl or $C_3$–$C_{18}$alkenyl or $C_3$–$C_{18}$alkinyl substituted by OH, halogen or a group —O—C(O)—$R_5$; $C_2$–$C_{18}$alkyl which is interrupted by O; $C_5$–$C_{12}$cycloalkyl; or phenyl; or $G_1$ and $G_2$ and/or $G_3$ and $G_4$ together with the linking carbon atom form a $C_6$–$C_{12}$cycloalkyl radical;

$Z_1$ is O or $NR_8$;

$R_8$ is hydrogen, OH, $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by one or more OH, halogen or a group —O—C(O)—$R_5$, $C_2$–$C_{18}$alkyl which is interrupted by at least one O atom and/or $NR_5$ group, $C_3$–$C_{12}$cycloalkyl or $C_6$–$C_{10}$aryl, $C_7$–$C_9$phenylalkyl, $C_5$–$C_{10}$heteroaryl, —C(O)—$C_1$–$C_{18}$alkyl, —O—$C_1$–$C_{18}$alkyl or —COO$C_1$–$C_{18}$alkyl;

Q is a direct bond or a divalent radical $CR_9R_{10}$, $CR_9R_{10}$—$CR_{11}R_{12}$, $CR_9R_{10}CR_{11}R_{12}CR_{13}R_{14}$, C(O) or $CR_9R_{10}C(O)$;

$R_9$, $R_{10}$, $R_{11}$, $R_{12}$, $R_{13}$ and $R_{14}$ are independently hydrogen, phenyl, or $C_1$–$C_{18}$alkyl;

T is $CH_2$—$C(R_{24})(R_{25})$—$CH_2$, wherein $R_{24}$ and $R_{25}$ together are =O or independently are H, OH or an organic residue, characterized in that the linking group T in total contains 2–500 carbon atoms and optionally 1–200 hetero atoms selected from, oxygen, phosphorus, sulfur, silicon, halogen and tertiary nitrogen. The N-oxyl educts of formulae B, III or IIIa are mostly known in the art; they may be prepared e.g. by the reaction of the corresponding N—H hindered amine with hydrogen peroxide and sodium tungstate as described by E. G. Rozantsev et al., in Synthesis, 1971, 192; or with tert-butyl hydroperoxide and molybdenum (VI) as taught in U.S. Pat. No. 4,691,015, or obtained in analogous manner.

The preferred amount of hydrocarbon for the instant process depends to some extent on the relative number of reactive hydrogens on the hydrocarbon reactant and the hindered amine nitroxyl compound. The reaction is typically carried out with a ratio of 1 to 100 moles of hydrocarbon per mole of nitroxyl moiety with the preferred ratio being 1 to 50 moles per mole of nitroxyl moiety, and the most preferred ratio being 1 to 30 moles of hydrocarbon per mole of nitroxyl moiety.

The preferred amount of organic hydroperoxide is 1 to 20 moles per mole of nitroxyl moiety, with the more preferred amount being 1 to 5 moles of peroxide per mole of nitroxyl moiety and the most preferred amount being 1 to 3 moles of peroxide per mole of nitroxyl moiety.

The organic hydroperoxide used in the process of present invention can be of the formula R—OOH, wherein R usually is a hydrocarbon containing 1–18 carbon atoms. The organic hydroperoxide preferably is a peroxoalcohol containing 3–18 carbon atoms. R is often aliphatic, preferably $C_1$–$C_{12}$alkyl. Most preferred organic hydroperoxide is tert-.butyl hydroperoxide.

The preferred amount of copper catalyst is from about 0.0001 to 0.5, especially 0.0005 to 0.1 molar equivalent per mole of nitroxyl moiety, with a ratio of 0.001 to 0.05 moles of metal or metal-ligand complex per mole of nitroxyl moiety being the most preferred.

The reaction is preferably run at 0° to 100° C.; more preferably at 20° to 100° C., especially in the range 20–80° C.

More specifically, the instant process involves the reaction of a mixture of 1 to 100 moles of the hydrocarbon of formula IV or V, 1 to 20 moles of organic hydroperoxide, and 0.001 mmoles to 0.5 moles of copper catalyst per mole of N-oxyl compound of formula B (1 mmol is 0.001 mol). Preferably, the molar ratio of copper catalyst per mole of N-oxyl compound of formula B is in the range from 1:100 to 1:100000, especially 1:300 to 1:100000.

E is preferably a carbon centered radical formed from a $C_7$–$C_{11}$phenylalkane or a $C_6$–$C_{10}$pyridylalkane; or $C_5$–$C_{12}$cycloalkane; or $C_5$–$C_{12}$cycloalkene; or an oxacyclohexane or oxycyclohexene; or $C_3$–$C_8$alkene; or $C_3$–$C_8$alkene substituted by phenoxy; or a benzene which is substituted by $C_1$–$C_4$alkyl and a further substituent selected from $C_1$–$C_4$alkoxy, glycidyl or glycidyloxy; or E is a radical of formula (VIII)

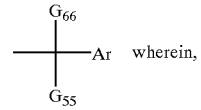

Ar is $C_6$–$C_{10}$aryl or $C_5$–$C_9$heteroaryl;
$G_{14}$ is $C_1$–$C_4$alkyl or an acyl radical of an aliphatic carboxylic acid containing 2 to 4 carbon atoms or benzoyl;
$G_{55}$ is H, $CH_3$ or phenyl;
$G_{66}$ is —CN or a group of the formula —$COOR_4$ or —$CH_2$—O—$G_{14}$;
$R_4$ is hydrogen or $C_1$–$C_8$alkyl;
L is a carbon centered radical formed from propane, butane, pentane, 2,2-dimethyl-propane, xylene.

Important are educts of formula IV or V which are pure hydrocarbons.

The educt of formula IV or V may serve two functions both as reactant and as solvent for the reaction. The reaction can also be carried out using an inert organic or inorganic solvent. A mixture of products may result if the hydrocarbon contains non-equivalent carbon-hydrogen bonds which are reactive in the instant process. For example, cyclohexane can give only one product whereas isopentane can give three distinct reaction products.

Usually the compound of formula IV or V reacts with its most active aliphatic carbon-hydrogen bond.

A solvent may be used, especially if the hydrocarbon of formula IV or V is a solid at the temperature of the reaction or if the catalyst is not very soluble in the hydrocarbon. Inert solvents should have less active carbon-hydrogen bonds; typical inert solvents are acetonitrile, aromatic hydrocarbons like benzene, chlorobenzene, $CCl_4$, alcohols (e.g. methanol, ethanol, ethylene glycol, ethylene glycol monomethyl ether), or, especially for reactions with activated hydrocarbons like alkylated aromats or alkenes, also alkanes like hexane, decane etc., or mixtures thereof. Inorganic solvents such as water are possible as well. The reaction can be carried out in one liquid phase or in separate phases.

Good results can be achieved when phase transfer catalysts such as quaternary ammonium or phosphonium salts are used in addition to the copper catalyst. Preferably, quaternary ammonium or phosphonium halogenides such as chlorides or bromides are employed for this purpose. The structure of the ammonium or phosphonium cation is less important; usually, quaternary ammonium or phosphonium cations contain 4 hydrocarbon residues bonded to the central nitrogen or phosphorus atom, which may be, for example, alkyl, phenylalkyl or phenyl groups. Some readily available materials are tetra-$C_1$–$C_{12}$alkylated. The phase transfer catalyst is preferably added in an amount from 0.0001 to 0.5, especially 0.001 to 0.1 molar equivalent per mole of nitroxyl moiety.

The copper catalyst used in the process of the invention is present mainly in the dissolved state. It is often an oxidizable complex ion in the lower oxidation state of a redox system $Cu^+/Cu^{2+}$ or $Cu^0/Cu^+$.

The ionic charges are counterbalanced by anionic ligands commonly known in complex chemistry of transition metals, such hydride ions ($H^-$) or anions derived from inorganic or organic acids, examples being halides, e.g. $F^-$, $Cl^-$, $Br^-$ or $I^-$, fluoro complexes of the type $BF_4^-$, $PF_6^-$, $SbF_6^-$ or $AsF_6^-$, anions of oxygen acids, alcoholates or acetylides or anions of cyclopentadiene.

Anions of oxygen acids are, for example, sulfate, phosphate, perchlorate, perbromate, periodate, antimonate, arsenate, nitrate, carbonate, the anion of a $C_1$–$C_8$carboxylic acid, such as formate, acetate, propionate, butyrate, benzoate, phenylacetate, mono-, di- or trichloro- or -fluoroacetate, sulfonates, for example methylsulfonate, ethylsulfonate, propylsulfonate, butylsulfonate, trifluoromethylsulfonate (triflate), unsubstituted or $C_1$–$C_4$alkyl-, $C_1$–$C_4$alkoxy- or halo-, especially fluoro-, chloro- or bromo-substituted phenylsulfonate or benzylsulfonate, for example tosylate, mesylate, brosylate, p-methoxy- or p-ethoxyphenylsulfonate, pentafluorophenylsulfonate or 2,4,6-triisopropylsulfonate, phosphonates, for example methylphosphonate, ethylphosphonate, propylphosphonate, butylphosphonate, phenylphosphonate, p-methylphenylphosphonate or benzylphosphonate, carboxylates derived from a $C_1$–$C_8$carboxylic acid, for example formate, acetate, propionate, butyrate, benzoate, phenylacetate, mono-, di- or trichloro- or -fluoroacetate, and also $C_1$–$C_{12}$-alcoholates, such as straight chain or branched $C_1$–$C_{12}$-alcoholates, e.g. methanolate or ethanolate. Also oxides are possible.

Anionic ligands and neutral may also be present up to the preferred coordination number of the complex cation, especially four, five or six. Additional negative charges are counterbalanced by cations, especially monovalent cations such as $Na^+$, $K^+$, $NH_4^+$ or $(C_1$–$C_4$ alkyl$)_4N^+$.

Suitable neutral ligands are inorganic or organic neutral ligands commonly known in complex chemistry of transition metals. They coordinate to the metal ion through a σ-, π-, μ-, η-type bonding or any combinations thereof up to the preferred coordination number of the complex cation. Suitable inorganic ligands are selected from the group consisting of aquo ($H_2O$), amino, nitrogen, carbon monoxide and nitrosyl. Suitable organic ligands are selected from the group consisting of phosphines, e.g. $(C_6H_5)_3P$, $(i$-$C_3H_7)_3P$, $(C_5H_9)_3P$ or $(C_6H_{11})_3P$, di-, tri-, tetra- and hydroxyamines, such as ethylenediamine, ethylenediaminotetraacetate (EDTA), N,N-Dimethyl-N',N'-bis(2-dimethylaminoethyl)-ethylenediamine (Me$_6$TREN), catechol, N,N'-dimethyl-1,2-benzenediamine, 2-(methylamino)phenol, 3-(methylamino)-2-butanol or N,N'-bis(1,1-dimethylethyl)-1,2-ethanediamine, N,N,N',N'',N''-pentamethyldiethyltriamine (PMDETA), $C_1$–$C_8$-glycols or glycerides, e.g. ethylene or propylene glycol or derivatives thereof, e.g. di-, tri- or tetraglyme, and monodentate or bidentate heterocyclic e$^-$ donor ligands.

Heterocyclic e$^-$ donor ligands are derived, for example, from unsubstituted or substituted heteroarenes from the group consisting of furan, thiophene, pyrrole, pyridine, bis-pyridine, picolylimine, g-pyran, g-thiopyran, phenanthroline, pyrimidine, bis-pyrimidine, pyrazine, indole, coumarone, thionaphthene, carbazole, dibenzofuran, dibenzothiophene, pyrazole, imidazole, benzimidazole, oxazole, thiazole, bis-thiazole, isoxazole, isothiazole, quinoline, bis-quinoline, isoquinoline, bis-isoquinoline, acridine, chromene, phenazine, phenoxazine, phenothiazine, triazine, thianthrene, purine, bis-imidazole and bis-oxazole.

The catalyst can be formed in a separate preliminary reaction step from its ligands or is preferably formed in-situ from its transition metal salt, e.g. Cu(I)Cl, which is then converted to the complex compound by addition of compounds corresponding to the ligands present in the complex catalyst, e.g. by addition of ethylenediamine, EDTA, Me$_6$TREN or PMDETA. These ligand complexes are items of commerce or may be formed in situ by mixing a metal salt with the ligand. The amount of ligand may be less than the amount required to completely complex the metal based on its oxidation state. The metal salt or metal-ligand complex may be bound to a solid support such as silica gel so that it can be recovered and reused.

Preferred is a process, wherein the active catalyst is a Cu(I) complex ion, especially in the Cu(I)/Cu(II) system.

The instant process can be run in air or in an inert atmosphere such a nitrogen or argon. The instant process can be run under atmospheric pressure as well as under reduced or elevated pressure. Elevated pressure can especially be useful in reactions with a hydrocarbon, which is gaseous under atmospheric pressure and the reaction temperature; in this case, pressure/temperature conditions are advantageous where the hydrocarbon forms a liquid phase or is at least partially dissolved in a suitable solvent.

There are several variations of the instant process. One variation involves the addition of a solution of organic hydroperoxide to a mixture of the N-oxyl hindered amine, the hydrocarbon and cosolvent (if used), and catalyst which has been brought to the desired temperature for reaction. The proper temperature may be maintained by controlling the rate of peroxide addition and/or by using a heating or cooling bath. After the hydroperoxide is added, the reaction mixture is conveniently stirred till the starting N-oxyl compound of formula III has disappeared or is no longer being converted to the compound of formula I and/or II. The reaction can be monitored by methods known in the art such as UV-Vis spectroscopy, thin layer chromatography, gas chromatography or liquid chromatography. Additional portions of catalyst can be added while the reaction is in progress. After the initial hydroperoxide charge has been added to the reaction mixture, more hydroperoxide can be added dropwise to bring the reaction to completion.

A second variation of the instant process is to simultaneously add separate solutions of the hydroperoxide and the nitroxyl compound to a mixture of the hydrocarbon, cosolvent (if used) and catalyst. The nitroxyl compound may be dissolved in water or the alcohol solvent used in the reaction. Some of the nitroxyl compound may be introduced into the reaction mixture prior to starting the peroxide addition, and all of the nitroxyl compound should be added prior to completing the peroxide addition.

Another variation of the instant process involves the simultaneous addition of separate solutions of the hydroperoxide and of the aqueous or alcohol solution of the catalyst to a mixture of the nitroxyl compound, hydrocarbon, and cosolvent (if used). Some of the metal may be introduced into the reaction mixture prior to starting the peroxide addition.

Still another variation of the instant process is the simultaneous addition of separate solutions of the hydroperoxide, of the aqueous or alcohol solution of the nitroxyl compound, and of an aqueous or alcohol solution of the catalyst to the hydrocarbon and cosolvent (if used). A portion of the nitroxyl compound and/or catalyst may be introduced into the reaction mixture prior to starting the hydroperoxide addition. All of the nitroxyl compound should be added prior to completing the hydroperoxide addition.

If a copper-ligand complex is prepared in situ, the metal salt and ligand are most effectively mixed prior to contact with the nitroxyl compound.

At the end of the reaction, the residual hydroperoxide should be carefully decomposed prior to the isolation of any products.

Examples for compounds which can be obtained advantageously with the process of present invention are those of formulae 1–28:

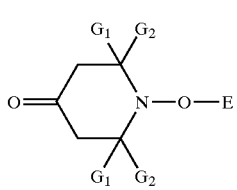

(1)

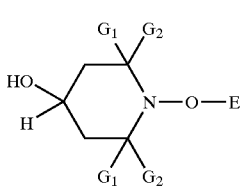

(2)

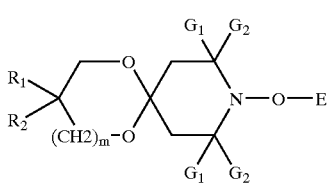

(3)

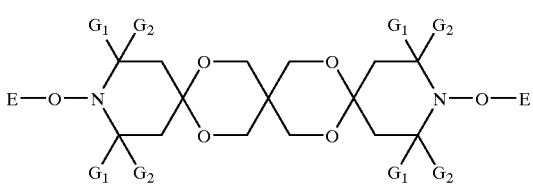

(4)

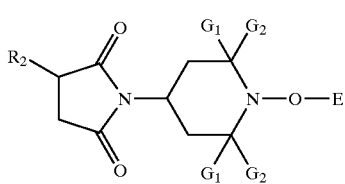

(5)

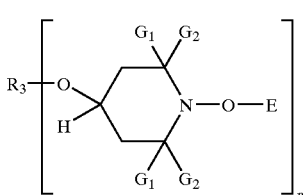

(6)

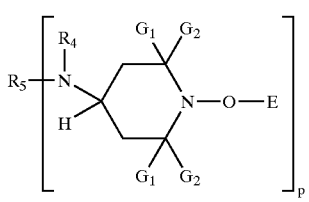

(7)

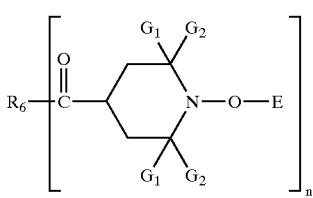

(8)

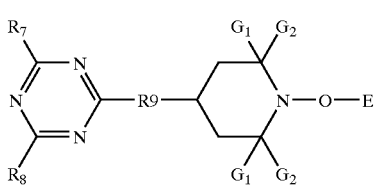

(9)

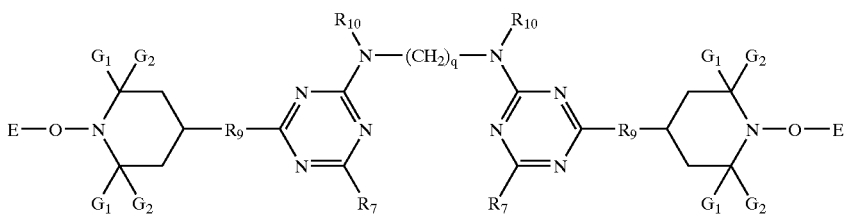

(10)

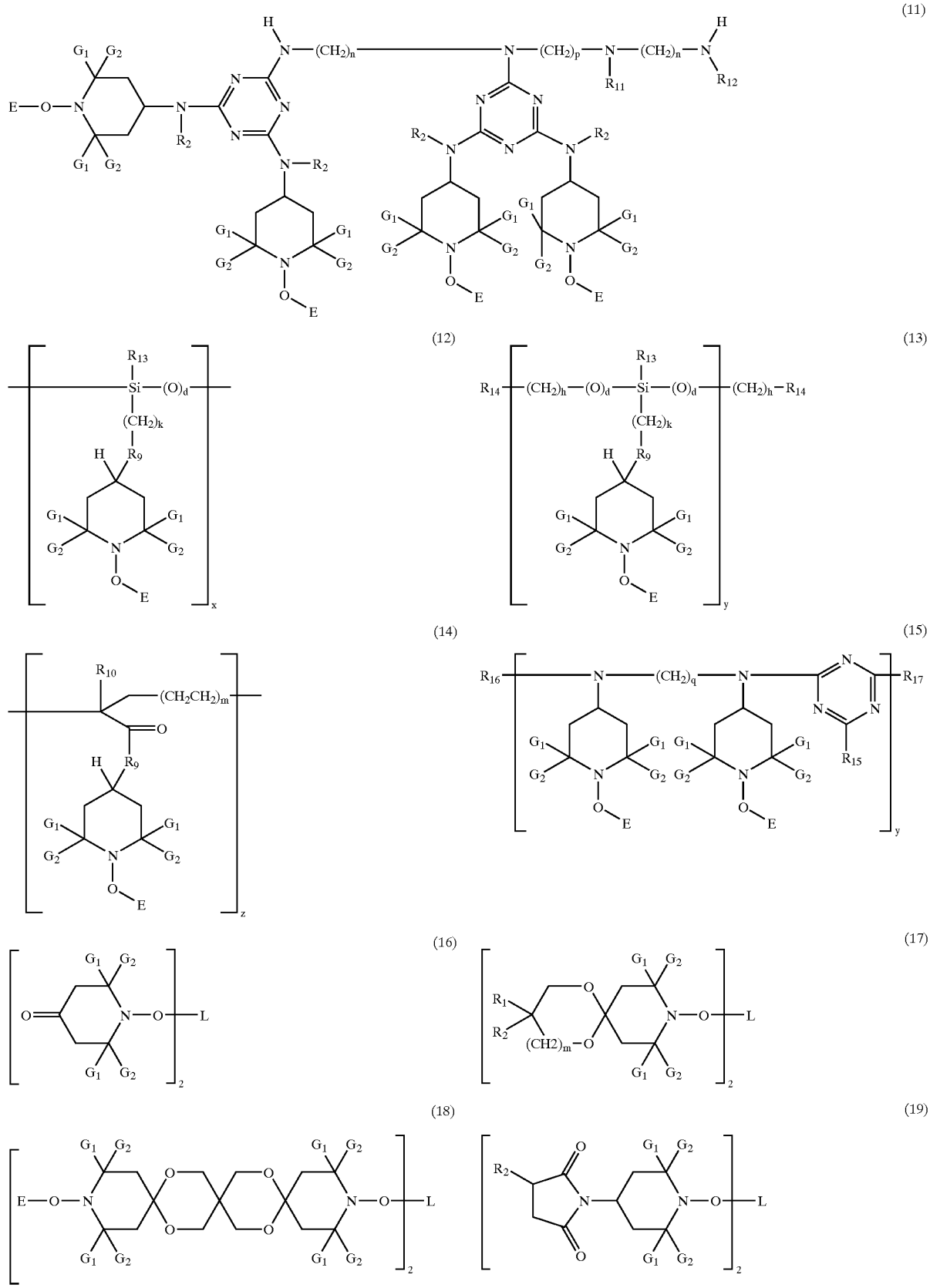

-continued

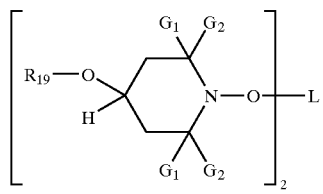
(20)

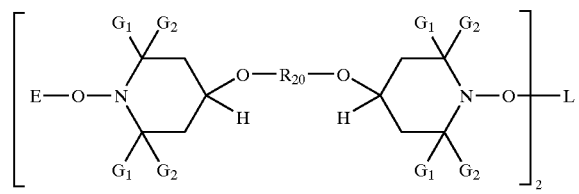
(21)

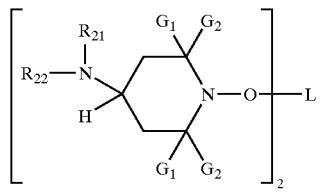
(22)

(23)

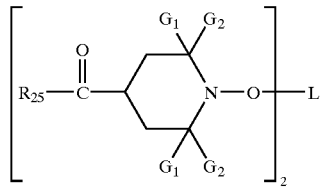
(24)

(25)

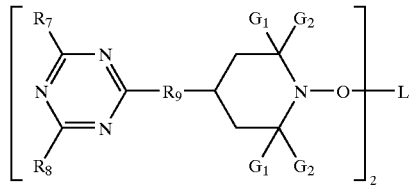
(26)

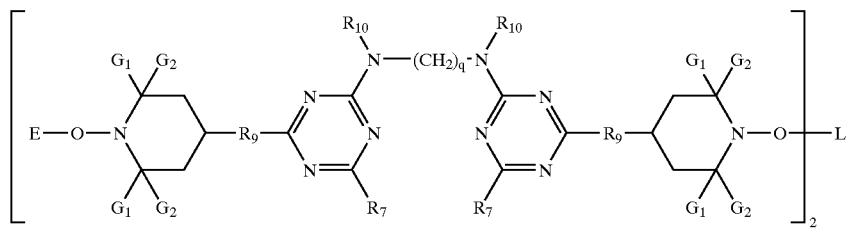
(27)

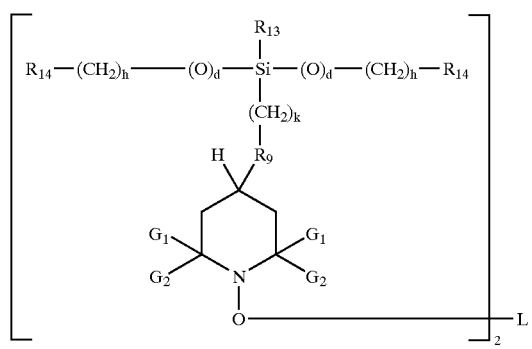
(28)

wherein in formulas (1) to (15):
  m is 0 or 1;
  $R_1$ is hydrogen, hydroxyl or hydroxymethyl;
  $R_2$ is hydrogen, alkyl of 1 to 12 carbon atoms or alkenyl of 2 to 12 carbon atoms;
  n is 1 to 4;
  when n is 1, $R_3$ is alkyl of 1 to 18 carbon atoms, alkoxycarbonylalkylenecarbonyl of 4 to 18 carbon atoms, alkenyl of 2 to 18 carbon atoms, glycidyl, 2,3-dihydroxypropyl, 2-hydroxy or 2-(hydroxymethyl) substituted alkyl of 3 to 12 carbon atoms which alkyl is interrupted by oxygen, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, or acyl radical of an aromatic acid containing 7 to 15 carbon atoms;

when n is 2, $R_3$ is alkylene of 2 to 18 carbon atoms, a divalent acyl radical of an aliphatic or unsaturated aliphatic dicarboxylic or dicarbamic acid containing 2 to 18 carbon atoms, a divalent acyl radical of a cycloaliphatic dicarboxylic or dicarbamic acid containing 7 to 12 carbon atoms, or a divalent acyl radical of an aromatic dicarboxylic acid containing 8 to 15 carbon atoms;

when n is 3, $R_3$ is a trivalent acyl radical of an aliphatic or unsaturated aliphatic tricarboxylic acid containing 6 to 18 carbon atoms, or a trivalent acyl radical of an aromatic tricarboxylic acid containing 9 to 15 carbon atoms;

when n is 4, $R_3$ is a tetravalent acyl radical of an aliphatic or unsaturated aliphatic tetracarboxylic acid, especially 1,2,3,4-butanetetracarboxylic acid, 1,2,3,4-but-2-enetetracarboxylic acid, 1,2,3,5-pentanetetracarboxylic acid and 1,2,4,5-pentanetetracarboxylic acid, or $R_3$ is a tetravalent acyl radical of an aromatic tetracarboxylic acid containing 10 to 18 carbon atoms;

p is 1 to 3, $R_4$ is hydrogen, alkyl of 1 to 18 carbon atoms or acyl of 2 to 6 carbon atoms;

when p is 1, $R_5$ is hydrogen, alkyl of 1 to 18 carbon atoms, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, an acyl radical of an aromatic carboxylic acid containing 7 to 15 carbon atoms, or $R_4$ and $R_5$ together are —$(CH_2)_5CO$—, phthaloyl or a divalent acyl radical of maleic acid;

when p is 2, $R_5$ is alkylene of 2 to 12 carbon atoms, a divalent acyl radical of an aliphatic or unsaturated aliphatic dicarboxylic or dicarbamic acid containing 2 to 18 carbon atoms, a divalent acyl radical of a cycloaliphatic dicarboxylic or dicarbamic acid containing 7 to 12 carbon atoms, or a divalent acyl radical of an aromatic dicarboxylic acid containing 8 to 15 carbon atoms;

when p is 3, $R_5$ is a trivalent acyl radical of an aliphatic or unsaturated aliphatic tricarboxylic acid containing 6 to 18 carbon atoms, or a trivalent acyl radical of an aromatic tricarboxylic acid containing 9 to 15 carbon atoms;

when n is 1, $R_6$ is alkoxy of 1 to 18 carbon atoms, alkenyloxy of 2 to 18 carbon atoms, —NHalkyl of 1 to 18 carbon atoms or —N(alkyl)$_2$ of 2 to 36 carbon atoms, when n is 2, $R_6$ is alkylenedioxy of 2 to 18 carbon atoms, alkenylenedioxy of 2 to 18 carbon atoms, —NH-alkylene-NH— of 2 to 18 carbon atoms or —N(alkyl)-alkylene-N(alkyl)- of 2 to 18 carbon atoms, or $R_6$ is 4-methyl-1,3-phenylenediamino, when n is 3, $R_6$ is a trivalent alkoxy radical of a saturated or unsaturated aliphatic triol containing 3 to 18 carbon atoms, when n is 4, $R_6$ is a tetravalent alkoxy radical of a saturated or unsaturated aliphatic tetraol containing 4 to 18 carbon atoms, $R_7$ and $R_8$ are independently chlorine, alkoxy of 1 to 18 carbon atoms, —O—$T_1$, amino substituted by 2-hydroxyethyl, —NH(alkyl) of 1 to 18 carbon atoms, —N(alkyl)$T_1$ with alkyl of 1 to 18 carbon atoms, or —N(alkyl)$_2$ of 2 to 36 carbon atoms, $R_9$ is oxygen, or $R_9$ is nitrogen substituted by either hydrogen, alkyl of 1 to 12 carbon atoms or $T_1$ $T_1$ is

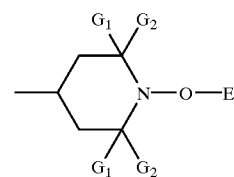

$R_{10}$ is hydrogen or methyl, q is 2 to 8, $R_{11}$ and $R_{12}$ are independently hydrogen or the group $T_2$

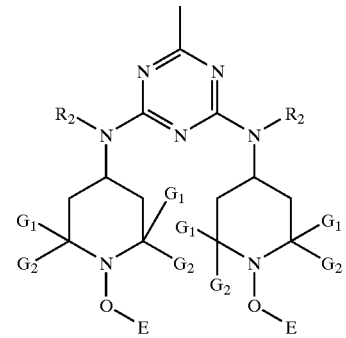

$R_{13}$ is hydrogen, phenyl, straight or branched alkyl of 1 to 12 carbon atoms, alkoxy of 1 to 12 carbon atoms, straight or branched alkyl of 1 to 4 carbon atoms substituted by phenyl, cycloalkyl of 5 to 8 carbon atoms, cycloalkenyl of 5 to 8 carbon atoms, alkenyl of 2 to 12 carbon atoms, glycidyl, allyloxy, straight or branched hydroxyalkyl of 1 to 4 carbon atoms, or silyl or silyloxy substituted three times independently by hydrogen, by phenyl, by alkyl of 1 to 4 carbon atoms or by alkoxy of 1 to 4 carbon atoms;

$R_{14}$ is hydrogen or silyl substituted three times independently by hydrogen, by phenyl, by alkyl of 1 to 4 carbon atoms or by alkoxy of 1 to 4 carbon atoms;

d is 0 or 1;

h is 0 to 4;

k is 0 to 5;

x is 3 to 6;

y is 1 to 10;

z is an integer such that the compound has a molecular weight of 1000 to 4000 amu, e.g. z may be from the range 3–10;

$R_{15}$ is morpholino, piperidino, 1-piperizinyl, alkylamino of 1 to 8 carbon atoms, especially branched alkylamino of 3 to 8 carbon atoms such as tert-octylamino, —N(alkyl)$T_1$ with alkyl of 1 to 8 carbon atoms, or —N(alkyl)$_2$ of 2 to 16 carbon atoms, $R_{16}$ is hydrogen, acyl of 2 to 4 carbon atoms, carbamoyl substituted by alkyl of 1 to 4 carbon atoms, s-triazinyl substituted once by chlorine and once by $R_{15}$, or s-triazinyl substituted twice by $R_{15}$ with the condition that the two $R_{15}$ substituents may be different;

$R_{17}$ is chlorine, amino substituted by alkyl of 1 to 8 carbon atoms or by $T_1$, —N(alkyl)$T_1$ with alkyl of 1 to 8 carbon atoms, —N(alkyl)$_2$ of 2 to 16 carbon atoms, or the group $T_3$

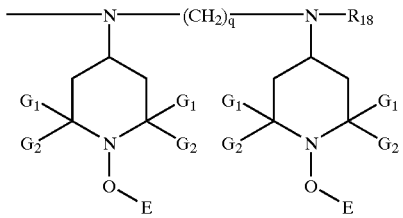

$R_{18}$ is hydrogen, acyl of 2 to 4 carbon atoms, carbamoyl substituted by alkyl of 1 to 4 carbon atoms, s-triazinyl substituted twice by —N(alkyl)$_2$ of 2 to 16 carbon atoms or s-triazinyl substituted twice by —N(alkyl)$T_1$ with alkyl of 1 to 8 carbon atoms;

in formulas (16) to (28), $R_1$, $R_2$, $R_7$, $R_8$, $R_9$, $R_{10}$, $R_{13}$, $R_{14}$, d, h, k, m, q, and $T_1$ have the same meanings as in formulas (1) to (15);

$R_{19}$ is hydrogen, alkyl of 1 to 18 carbon atoms, alkenyl of 2 to 18 carbon atoms, glycidyl, 2,3-dihydroxypropyl, 2-hydroxy or 2-(hydroxymethyl) substituted alkyl of 3 to 12 carbon atoms which alkyl is interrupted by oxygen, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, or acyl radical of an aromatic acid containing 7 to 15 carbon atoms;

$R_{20}$ is alkylene of 2 to 18 carbon atoms, a divalent acyl radical of an aliphatic or unsaturated aliphatic dicarboxylic or dicarbamic acid containing 2 to 18 carbon atoms, a divalent acyl radical of a cycloaliphatic dicarboxylic or dicarbamic acid containing 7 to 12 carbon atoms, or a divalent acyl radical of an aromatic dicarboxylic acid containing 8 to 15 carbon atoms;

$R_{21}$ is hydrogen, alkyl of 1 to 18 carbon atoms or acyl of 2 to 6 carbon atoms;

$R_{22}$ is hydrogen, alkyl of 1 to 18 carbon atoms, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, an acyl radical of an aromatic carboxylic acid containing 7 to 15 carbon atoms, or $R_4$ and $R_5$ together are —(CH$_2$)$_5$CO—, phthaloyl or a divalent acyl radical of maleic acid;

$R_{23}$ is hydrogen, alkyl of 1 to 4 carbon atoms or acyl of 2 to 6 carbon atoms;

$R_{24}$ is alkylene of 2 to 18 carbon atoms, a divalent acyl radical of an aliphatic or unsaturated aliphatic dicarboxylic or dicarbamic acid containing 2 to 18 carbon atoms, a divalent acyl radical of a cycloaliphatic dicarboxylic or dicarbamic acid containing 7 to 12 carbon atoms, or a divalent acyl radical of an aromatic dicarboxylic acid containing 8 to 15 carbon atoms;

$R_{25}$ is alkoxy of 1 to 18 carbon atoms, alkenyloxy of 2 to 18 carbon atoms, —NHalkyl of 1 to 18 carbon atoms or —N(alkyl)$_2$ of 2 to 36 carbon atoms, $R_{26}$ is alkylenedioxy of 2 to 18 carbon atoms, alkenylenedioxy of 2 to 18 carbon atoms, —NH-alkylene-NH— of 2 to 18 carbon atoms or —N(alkyl)-alkylene-N(alkyl)- of 3 to 18 carbon atoms.

E is a carbon centered radical formed preferably from a $C_7$–$C_{11}$phenylalkane, especially toluene, ethylbenzene, isopropylbenzene; or $C_5$–$C_{12}$cycloalkane, especially cyclohexene; or $C_5$–$C_{12}$cycloalkene, especially cyclohexene; or $C_3$–$C_8$alkene, especially propene; or a benzene which is substituted by $C_1$–$C_4$alkyl and a further substituent selected from $C_1$–$C_4$alkoxy, glycidyl or glycidyloxy.

L is a carbon centered radical formed preferably from propane, butane, pentane, 2,2-dimethyl-propane, xylene, diethylbenzene.

Preferably, the reaction site in the compound E—H or H—L—H is an activated carbon-hydrogen bond, whose carbon, for example, is linked to an electron pushing functional group or a functional group able to stabilize the radical formed after cleavage of the carbon-hydrogen bond. Electron withdrawing groups, if present in E—H or H—L—H, are preferably not directly linked to the reactive site.

Some compounds obtainable by the instant process are novel compounds. Thus, another object of the invention is a compound of the formula XV or XVI

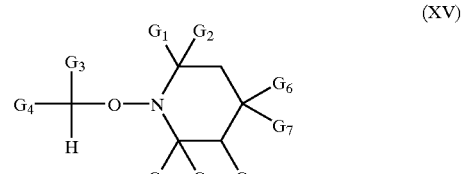

(XV)

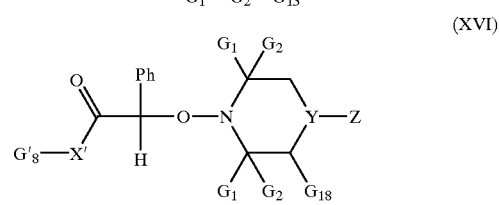

(XVI)

wherein $G_1$ and $G_2$ independently are methyl or ethyl;

$G_3$ is $C_2$–$C_8$alkenyl; $C_2$–$C_8$alkenyl substituted by phenyl, $C_1$–$C_4$alkyl-phenyl, cyclohexyl, $C_1$–$C_4$alkyl-cyclohexyl or COX'$G_8$; or $G_3$ is OG$_{10}$; or is a carbon-bonded 5- or 6-membered unsubstituted or alkyl substituted heterocyclic residue containing 3–12 carbon atoms, especially 5 carbon atoms in total and whose heteroatoms are selected from nitrogen and oxygen;

$G_4$ is as defined for $G_3$ or is $C_1$–$C_{18}$alkyl, provided that $G_4$ is not methyl when $G_3$ is $C_2$-alkenyl; or $G_3$ and $G_4$ together with the carbon atom they are attached to form the residue Ph—CH—CN, or form a carbon-bonded 5- or especially 6-membered unsubstituted or possibly alkyl substituted, unsaturated heterocyclic residue containing 3–12 carbon atoms in total, especially 5 carbon atoms in total, whose heteroatoms are selected from nitrogen and oxygen;

$G_6$ is H; OH; OR$_3$; NR$_4$R$_5$; (CO)R$_6$; or is a radical of formula

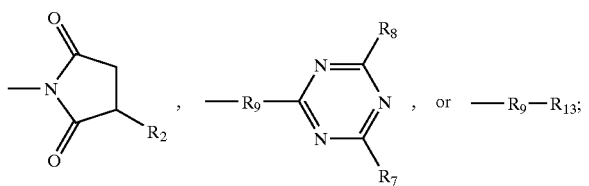

$G_7$ is H;
or $G_6$ and $G_7$ together are =O or a residue of formula
—O—CH$_2$—C(R$_1$)(R$_2$)—(CH$_2$)$_m$—O—;
$G_8$ is hydrogen or $C_1$–$C_8$alkyl or $C_2$–$C_8$hydroxyalkyl, especially $C_1$–$C_8$alkyl;
$G'_8$ is hydrogen or $C_1$–$C_8$alkyl or $C_2$–$C_8$hydroxyalkyl or $C_2$–$C_8$alkenyl; $G_{10}$ is $C_1$–$C_{18}$alkyl; $C_1$–$C_{18}$alkyl substituted by phenyl or $C_1$–$C_{12}$alkyl, $C_1$–$C_{12}$alkoxy and/or OH substituted phenyl; phenyl; phenyl substituted by $C_1$–$C_{12}$alkyl, $C_1$–$C_{12}$alkoxy, OH; or is a carbon-bonded 5- or 6-membered unsubstituted or alkyl substituted heterocyclic residue containing 3–12 carbon atoms and whose heteroatoms are selected from nitrogen and oxygen;
$G_{15}$ is H or methyl;
$G_{16}$ is OH; OR$_3$; NR$_4$R$_5$; (CO)R$_6$; or is a radical of formula

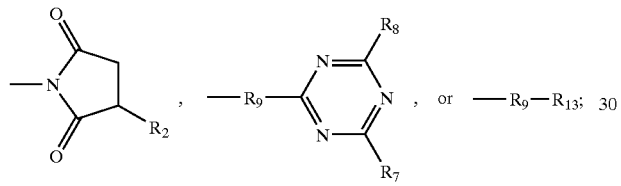

$G_{17}$ is H;
or $G_{16}$ and $G_{17}$ together are =O or a residue of formula
—O—CH$_2$—C(R$_1$)(R$_2$)—(CH$_2$)$_m$—O—;
$G_{18}$ is H or methyl or =O;
Ph is phenyl or phenyl substituted by $C_1$–$C_4$alkyl, $C_1$–$C_4$alkoxy, halogen and/or nitro;
m is 0 or 1;
$R_1$ is hydrogen, $C_1$–$C_4$alkyl, hydroxyl or hydroxymethyl;
$R_2$ is hydrogen, alkyl of 1 to 12 carbon atoms or alkenyl of 2 to 12 carbon atoms;
$R_3$ is alkyl of 1 to 18 carbon atoms, alkoxycarbonylalkylenecarbonyl of 4 to 18 carbon atoms, alkenyl of 2 to 18 carbon atoms, glycidyl, 2,3-dihydroxypropyl, 2-hydroxy or 2-(hydroxymethyl) substituted alkyl of 3 to 12 carbon atoms which alkyl is interrupted by oxygen, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, or acyl radical of an aromatic acid containing 7 to 15 carbon atoms;
$R_4$ is hydrogen, alkyl of 1 to 18 carbon atoms or acyl of 2 to 6 carbon atoms;
$R_5$ is hydrogen, alkyl of 1 to 18 carbon atoms, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, an acyl radical of an aromatic carboxylic acid containing 7 to 15 carbon atoms, or $R_4$ and $R_5$ together are —(CH$_2$)$_5$CO—, phthaloyl or a divalent acyl radical of maleic acid;
$R_6$ is alkoxy of 1 to 18 carbon atoms, alkenyloxy of 2 to 18 carbon atoms, —NHalkyl of 1 to 18 carbon atoms or —N(alkyl)$_2$ of 2 to 36 carbon atoms;

$R_7$ and $R_8$ are independently chlorine, alkoxy of 1 to 18 carbon atoms, amino substituted by 2-hydroxyethyl, —NH(alkyl) of 1 to 18 carbon atoms, or —N(alkyl)$_2$ of 2 to 36 carbon atoms;
$R_9$ is oxygen, or $R_9$ is nitrogen substituted by hydrogen or alkyl of 1 to 12 carbon atoms;
$R_{13}$ is silyl or silyloxy substituted three times independently by hydrogen, by phenyl, by alkyl of 1 to 4 carbon atoms or by alkoxy of 1 to 4 carbon atoms;
$R_{30}$ is H, $C_1$–$C_{18}$alkyl, $C_5$–$C_{12}$cycloalkyl, $C_3$–$C_{18}$alkoxyalkyl;
X' is O or NG$_8$;
Y—Z is >C(G$_{17}$)G$_{16}$ or O or >N—R$_{30}$.

Another object of the invention is compound of the formula XVII or XVIII

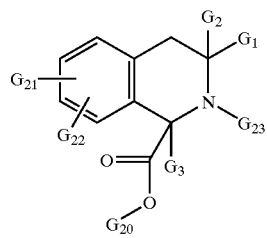

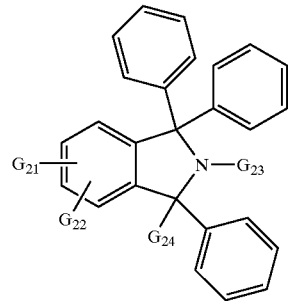

wherein
$G_1$, $G_2$ and $G_3$ are independently methyl or ethyl;
$G_{20}$ is H, $C_1$–$C_{18}$alkyl or $C_5$–$C_{12}$cycloalkyl, especially $C_1$–$C_{12}$alkyl;
$G_{21}$ and $G_{22}$ are independently hydrogen, halogen, $C_1$–$C_{12}$alkyl or $C_1$–$C_{12}$alkoxy;
$G_{23}$ is oxyl, OH or OE, where E is as defined in claim 1;
$G_{24}$ is methyl, ethyl or phenyl.
Preferred is a compound of the formula XV

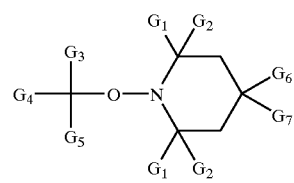

wherein
$G_1$ and $G_2$ independently are methyl or ethyl;
$G_3$ is $C_2$–$C_8$alkenyl; $C_2$–$C_8$alkenyl substituted by phenyl, $C_1$–$C_4$alkyl-phenyl, cyclohexyl, $C_1$–$C_4$alkyl-cyclohexyl or COX'G$_8$; OG$_{10}$; or is a carbon-bonded 5- or 6-membered unsubstituted or alkyl substituted heterocyclic residue containing 3–12 carbon atoms and whose heteroatoms are selected from nitrogen and oxygen;

$G_4$ is as defined for $G_3$ or is $C_1$–$C_{18}$alkyl;

or $G_3$ and $G_4$ together with the carbon atom they are attached to form a carbon-bonded 5- or 6-membered unsubstituted or alkyl substituted heterocyclic residue containing 3–12 carbon atoms, whose heteroatoms are selected from nitrogen and oxygen;

$G_5$ is hydrogen;

$G_6$ is H; OH; $OR_3$; $NR_4R_5$; $(CO)R_6$; or is a radical of formula

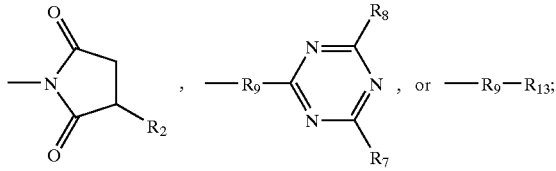

$G_7$ is H;

or $G_6$ and $G_7$ together are =O or a residue of formula —O—$CH_2$—$C(R_1)(R_2)$—$(CH_2)_m$—O—;

$G_8$ is hydrogen or $C_1$–$C_8$alkyl or $C_2$–$C_8$hydroxyalkyl;

$G_{10}$ is $C_1$–$C_{18}$alkyl; $C_1$–$C_{18}$alkyl substituted by phenyl or $C_1$–$C_{12}$alkyl, $C_1$–$C_{12}$alkoxy and/or OH substituted phenyl; phenyl; phenyl substituted by $C_1$–$C_{12}$alkyl, $C_1$–$C_{12}$alkoxy, OH; or is a carbon-bonded 5- or 6-membered unsubstituted or alkyl substituted heterocyclic residue containing 3–12 carbon atoms and whose heteroatoms are selected from nitrogen and oxygen;

m is 0 or 1;

$R_1$ is hydrogen, hydroxyl or hydroxymethyl;

$R_2$ is hydrogen, alkyl of 1 to 12 carbon atoms or alkenyl of 2 to 12 carbon atoms;

$R_3$ is alkyl of 1 to 18 carbon atoms, alkoxycarbonylalkylenecarbonyl of 4 to 18 carbon atoms, alkenyl of 2 to 18 carbon atoms, glycidyl, 2,3-dihydroxypropyl, 2-hydroxy or 2-(hydroxymethyl) substituted alkyl of 3 to 12 carbon atoms which alkyl is interrupted by oxygen, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, or acyl radical of an aromatic acid containing 7 to 15 carbon atoms;

$R_4$ is hydrogen, alkyl of 1 to 18 carbon atoms or acyl of 2 to 6 carbon atoms;

$R_5$ is hydrogen, alkyl of 1 to 18 carbon atoms, an acyl radical of an aliphatic or unsaturated aliphatic carboxylic or carbamic acid containing 2 to 18 carbon atoms, an acyl radical of a cycloaliphatic carboxylic or carbamic acid containing 7 to 12 carbon atoms, an acyl radical of an aromatic carboxylic acid containing 7 to 15 carbon atoms, or $R_4$ and $R_5$ together are —$(CH_2)_5$CO—, phthaloyl or a divalent acyl radical of maleic acid;

$R_6$ is alkoxy of 1 to 18 carbon atoms, alkenyloxy of 2 to 18 carbon atoms, —NHalkyl of 1 to 18 carbon atoms or —N(alkyl)$_2$ of 2 to 36 carbon atoms;

$R_7$ and $R_8$ are independently chlorine, alkoxy of 1 to 18 carbon atoms, amino substituted by 2-hydroxyethyl, —NH(alkyl) of 1 to 18 carbon atoms, or —N(alkyl)$_2$ of 2 to 36 carbon atoms;

$R_9$ is oxygen, or $R_9$ is nitrogen substituted by hydrogen or alkyl of 1 to 12 carbon atoms;

$R_{13}$ is silyl or silyloxy substituted three times independently by hydrogen, by phenyl, by alkyl of 1 to 4 carbon atoms or by alkoxy of 1 to 4 carbon atoms;

X' is O or NH.

Preferred compounds are those wherein the carbon-bonded 5- or 6-membered unsubstituted or alkyl substituted heterocyclic residue containing 3–12 carbon atoms, whose heteroatoms are selected from nitrogen and oxygen, is pyridyl; furyl; di- or tetrahydrofuryl; pyryl; di- or tetrahydropyryl; dioxanyl; or one of these residues substituted by $C_1$–$C_4$alkyl. Further preferences are as described above for formula A.

Compounds of the formula A and XV can be employed with advantage for stabilizing organic material against the damaging effect of light, oxygen and/or heat, especially for stabilizing synthetic organic polymers or compositions containing them. They are notable for high thermal stability, substrate compatibility and good persistence in the substrate. Examples of polymers which can be stabilized in this way are the following:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethyleneibut-1-ene copolymers, ethylene/hexene copolymers, ethylene/methylpentene copolymers, ethylene/heptene copolymers, ethylene/octene copolymers, propylene/ butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/ styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 619, 6/12, 416, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.
26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
27. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Of particular interest is the use of compounds of the formula XV as stabilizers in synthetic organic polymers, for example a coating or a bulk polymer or article formed therefrom, especially in thermoplastic polymers and corresponding compositions as well as in coating compositions. Thermoplastic polymers of most importance in present compositions are polyolefines and their copolymers, such as listed above under items 1–3, thermoplastic polyolefin (TPO), thermoplastic polyurethan (TPU), thermoplastic rubber (TPR), polycarbonate, such as in item 19 above, and blends, such as in item 28 above. Of utmost importance are polyethylene (PE), polypropylene (PP), polycarbonate (PC) and polycarbonate blends such as PC/ABS blends, as well as in acid or metal catalyzed coating compositions.

In general the compounds of present invention are added to the material to be stabilized in amounts of from 0.1 to 10%, preferably from 0.01 to 5%, in particular from 0.01 to 2% (based on the material to be stabilized). Particular preference is given to the use of the novel compounds in amounts of from 0.05 to 1.5%, especially from 0.1 to 0.5%. Where compounds of present invention are used as flame retardants, dosages are usually higher, e.g. 0.1 to 25% by weight, mainly 0.1 to 10% by weight of the organic material to be stabilized and protected against inflammation.

Used in polymerizable compositions as a polymerization regulator or initiator, preferably the regulator/initiator compound is present in an amount of from 0.01 mol-% to 30 mol-%, more preferably in an amount of from 0.1 mol-% to 20 mol-% and most preferred in an amount of from 0.5 mol-% to 10 mol-% based on the monomer or monomer mixture.

Incorporation into the materials can be effected, for example, by mixing in or applying the compounds of the formula A or XV and, if desired, further additives by the methods which are customary in the art. Where polymers are involved, especially synthetic polymers, incorporation can take place prior to or during the shaping operation, or by applying the dissolved or dispersed compound to the polymer, with or without subsequent evaporation of the solvent. In the case of elastomers, these can also be stabilized as latices. A further possibility for incorporating the compounds of the formula XV into polymers is to add them before, during or directly after the polymerization of the corresponding monomers or prior to crosslinking. In this context the compound of the formula XV can be added as it is or else in encapsulated form (for example in waxes, oils or polymers). In the case of addition prior to or during the polymerization, the compounds of the formula XV can also act as a regulator of the chain length of the polymers (chain terminator).

The compounds of the formula XV can also be added in the form of a masterbatch containing said compound in a concentration, for example, of from 2.5 to 25% by weight to the polymers that are to be stabilized.

The compounds of the formula XV can judiciously be incorporated by the following methods:
- as emulsion or dispersion (e.g. to latices or emulsion polymers),
- as a dry mixture during the mixing in of additional components or polymer mixtures,
- by direct introduction into the processing apparatus (e.g. extruders, internal mixers, etc),
- as solution or melt.

Novel polymer compositions can be employed in various forms and/or processed to give various products, for example as (to give) films, fibres, tapes, moulding compositions, profiles, or as binders for coating materials, adhesives or putties.

In addition to the compounds of the formula XV the novel compositions may as additional component C comprise one or more conventional additives such as, for example, those indicated below.

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'- methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl4-hydroxy-2-methylphenyl)butane, 2,6-bis(3-tert-butyl-5-methyl-2-hydroxybenzyl)4-methylphenol, 1,1,3-tris(5-tert-butyl-4-hydroxy-2-methylphenyl)butane, 1,1-bis(5-tert-butyl4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl) pentane.

1.7. O—, N— and S-benzyl compounds, for example 3,5, 3',5'-tetra-tert-butyl4,4'-dihydroxydibenzyl ether, octadecyl-4-hydroxy-3,5-dimethylbenzylmercaptoacetate, tridecyl4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, didodecylmercaptoethyl-2,2-bis-(3,5-di-tert-butyl4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto4,6-bis(3,5-di-tert-butyl-4-hydroxyanilino)-1,3,5-triazine, 2-octylmercapto-4,6-bis (3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl) isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl) isocyanurate.

1.11. Benzylphosphonates, for example dimethyl-2,5-di-tert-butyl4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.14. Esters of β-(5-tert-butyl4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.15. Esters of β-(3,5-dicyclohexyl4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.16. Esters of 3.5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.17. Amides of β-(3,5-di-tert-butyl4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl4-hydroxyphenylpropionyl)-hydrazide, N,N'-bis[2-(3-[3,5-di-tert-butyl4-hydroxyphenyllpropionyloxy) ethyldoxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyidiphenylamines, a mixture of mono- and dialkylated isopropylisohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)pheny!)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy 5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-12-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis-(4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$ where R=3'-tert-butyl4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octyiphenyl salicylate, dibenzoyl resorcinol, bis(4-tert-butylbenzoyl) resorcinol, benzoyl resorcinol, 2,4-di-tert-butylphenyl 3,5-di-tert-butyl4-hydroxybenzoate, hexadecyl 3,5-di-tert-butyl4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl) hexamethylenediamine and 4-morpholino-2,6-dichloro-1,3,5-triazine, the condensate of 2-chloro4,6-bis(4-n-butylamino-2,2,6,6-tetramethylpiperidyl )-1,3,5-triazine and 1,2-bis(3-aminopropylamino)ethane, the condensate of 2-chloro4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino) ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4- piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxyarbonyl)-2-(4-methoxyphenyl)ethene, N,N'-bis-formyl-N,N'-bis(2,2,6,6-tetramethyl-4-piperidyl) hexamethylenediamine, diester of 4-methoxy-methylene-malonic acid with 1,2,2,6,6-pentamethyl-4-hydroxypiperidine, polylmethylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine4-yl)-N-butyl-amino]-6-(2-hydroxyethyl)amino-1,3,5-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis-(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-5,3,5-triazine, 2-[4-(dodecyloxyltridecyloxy-2-hydroxypropoxy)-2-hydroxy-phenyl]4,6-bis(2,4-dimethylphenyl)-1,3,5-triazine, 2-[2-hydroxy4-(2-hydroxy-3-dodecyloxy-propoxy)phenyl]4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2-{2-hydroxy4-[1-octyloxycarbonyl-ethoxy]phenyl}-4,6-bis(4-phenylphenyl)-1,3,5Sriazine wherein the octyl moiety is a mixture of different isomers.

3. Metal deactivators, for example N,N'-diphenyloxamide, N-salicylal-N'-salicyloyl hydrazine, N, N'-bis(salicyloyl) hydrazine, N, N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo(triethyltris(3,3',5,5'-tetra-tert-butyl-1,1'-biphenyl-2,2'-diyl)phosphitel, 2-ethylhexyl(3,3',5,5'-tetra-tert-butyl-1,1'-biphenyl-2,2'-diyl)phosphite.

Especially preferred are the following phosphites:
Tris(2,4-di-tert-butylphenyl) phosphite (Irgafos® 168, Ciba-Geigy), tris(nonylphenyl) phosphite,

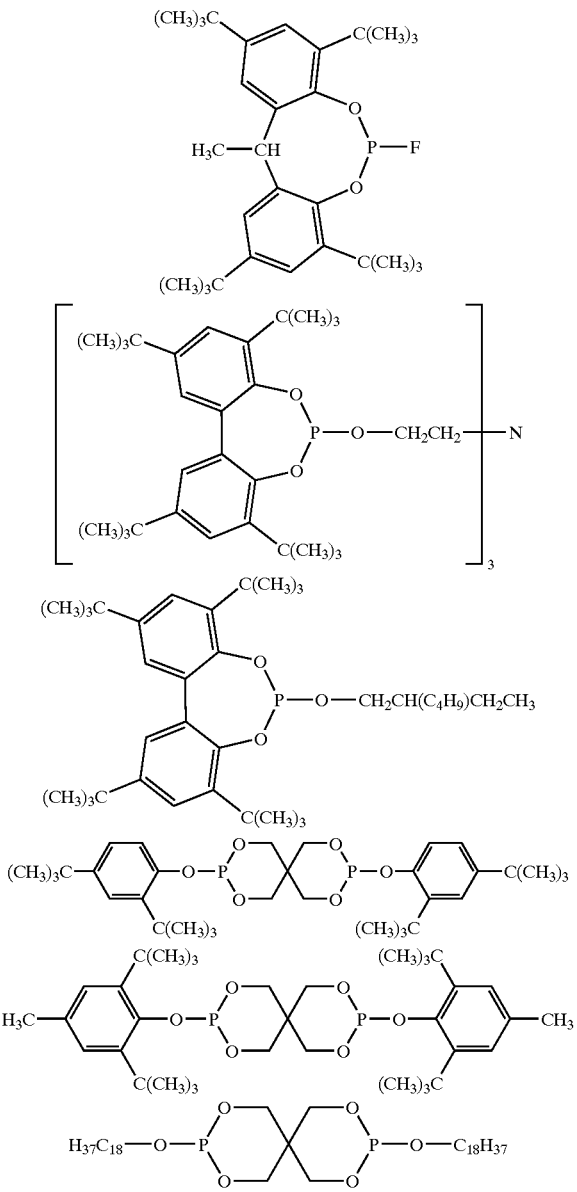

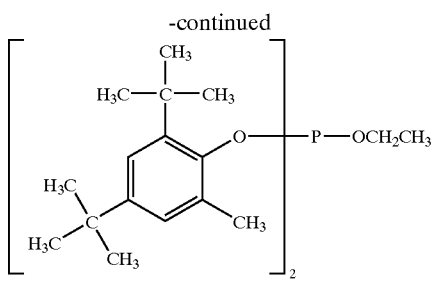

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxyiamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhy-droxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl4-pivaloyloxyphenyl)-5,7-di-tert-butyl-benzofuran-2-one, 3-(3,4-dimethylphenyl)-5,7-di-tert-butyl-benzofuran-2-one, 3-(2,3-di-methylphenyl)-5,7-di-tert-butyl-benzofuran-2-one.

The conventional additives are judiciously employed in amounts of 0.1–10% by weight, for example 0.2–5% by weight, based on the material to be stabilized.

The following examples are for illustrative purposes only and are not to be construed to limit the instant invention in any manner whatsoever. Percentages given are usually percent by weight if not otherwise indicated. Abbreviations used:

min. minutes;

HPLC high pressure liquid chromatography;

GC gas chromatography.

EXAMPLE 1

Preparation of

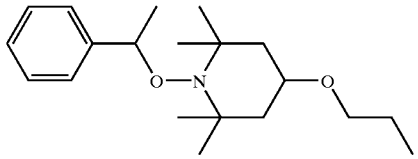

A mixture of 0.85 ml 1-oxyl-2,2,6,6-tetramethyl-4-propoxypiperidine, 4.67 ml of a 53.4% solution of tert.butyl hydroperoxide in decane, and 25 mg CuCl$_2$ (as a 1% solution in ethanol; ratio catalyst:nitroxyl=1:2000 {mol/mol}) and 4.95 g ethylbenzene is stirred at 60° C. After 60 min., the reaction is terminated by pouring the mixture into 30 ml of a solution of 10% Na$_2$SO$_3$ in water. The flask is washed twice with 20 ml ethyl acetate in total, which is added to the water/reaction mixture. The organic layer is separated and washed twice with 40 ml water in total. Distillation of solvent yields 1.46 g (97% of theory) of the above product (purity 95%, GC).

EXAMPLE 2

Preparation of

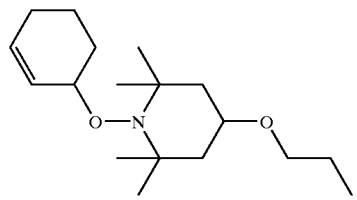

A mixture of 0.85 ml 1-oxyl-2,2,6,6-tetramethyl-4-propoxypiperidine, 4.67 ml of a 53.4% solution of tert.butyl hydroperoxide in decane, 25 mg CuCl$_2$ (as a 1% solution in ethanol) and 3.83 g cyclohexene is stirred at 60° C. After 12 min., the reaction is terminated and the product recovered as described in example 1. Distillation of solvent yields 1.05 g (95% of theory) of the above product (purity more than 98%, GC).

EXAMPLE 3

Preparation of

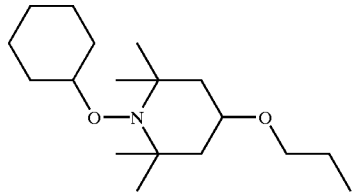

A mixture of 0.85 ml 1-oxyl-2,2,6,6-tetramethyl-4-propoxypiperidine, 4.67 ml of a 53.4% solution of tert.butyl hydroperoxide in decane, 100 mg $CuCl_2$ (as a 1% solution in ethanol) and 3.92 g cyclohexane is stirred at 60° C. After 200 min., the reaction is terminated and the product recovered as described in example 1. Distillation of solvent yields 0.90 g (81% of theory) of the above product.

EXAMPLES 4–8

Preparation of

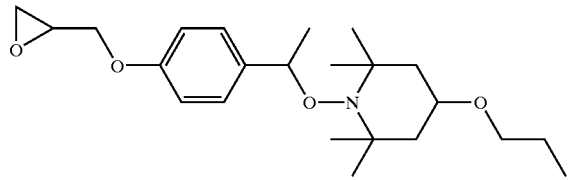

To a mixture of 0.53 ml 1-oxyl-2,2,6,6-tetramethyl-4-propoxypiperidine (=1 equivalent), 2.92 ml of a 53.4% solution of tert.butyl hydroperoxide in decane (6 equivalents), and 3.96 ml (10 equivalents) of 4-glycidyloxy-1-ethylbenzene, $10^{-3}$ equivalents of the catalyst indicated in the following table are added as as a 1% b.w. solution in ethanol. Examples 7 and 8 are carried out using iron instead of copper catalysts for comparison purposes. The mixture is stirred at 60° C. for the reaction time indicated. Subsequently, the reaction is terminated by pouring the mixture into 30 ml of a solution of 10% $Na_2SO_3$ in water. The flask is washed twice with 20 ml of ethyl acetate in total, which is added to the water/reaction mixture. The organic layer is separated and washed twice with 40 ml of water in total. The above product is isolated by distillation; catalysts, reaction time and yields are given in the following table 1.

TABLE 1

Yield and reaction times using copper or iron catalysts

| Example | Catalyst | Reaction Time | Yield |
|---|---|---|---|
| 4 | CuCl | 20 min. | 85% |
| 5 | CuCl | 20 min. | 85% |
| 6 | $CuCl_2$ | 20 min. | 83% |
| 7 (comparison) | $FeCl_2$ | 180 min. | 5% |
| 8 (comparison) | $FeBr_3$ | 180 min. | 6% |

The enormous advantage achievable by the use of a copper catalyst is evident.

EXAMPLE 9

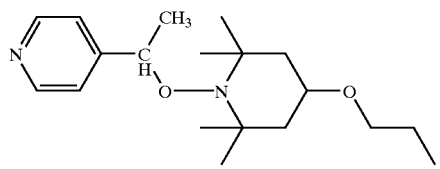

A mixture of 0.85 ml 1-oxyl-2,2,6,6-tetramethyl4-propoxypiperidine, 4.67 ml of a 53.4% solution of tert.butyl hydroperoxide in decane, 25 mg $CuCl_2$ (as a 1% solution in ethanol; giving a ration catalyst:educt=1:2000) and 5.00 g 4-ethylpyridine is stirred at 60° C. for 2.5 h. The reaction mixture is poured into 30 ml of a solution of 10% by weight of $Na_2SO_3$ in water, the flask washed twice with 10 ml of ethyl acetate, respectively, and these washings are added to the aqueous reaction mixture. Separating the organic layer, washing twice with water (2×20 ml) and distillation yields 1.46 g (97% of theory) of the above product, purity 95% (GC).

EXAMPLE 10

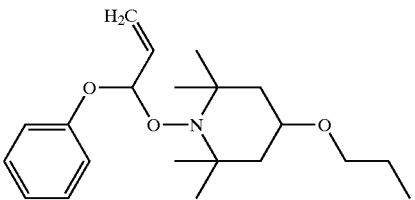

Reaction is performed as described in Example 9, with 6.26 g of allyl-phenyl-ether instead of 4-ethylpyridine. This yields 1.56 g (96%) of the above product, purity >98% (GC).

EXAMPLE 11

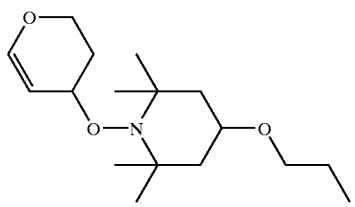

Reaction is performed as described in Example 9, with 3.91 g of 3,4-dihydro-2H-pyran instead of 4-ethylpyridine and termination of reaction after 8 minutes. This yields 1.12 g (100%) of the above product.

EXAMPLE 12

Preparation of 1-(1-phenylethyl)oxy-2,2,6,6-tetramethylpiperidine

A mixture of 0.5 g (3.2 mmol; 1 eq.) 1-oxyl-2,2,6,6-tetramethylpiperidine (TEMPO), 1.24 g of a 70% aq. solution of tert.butyl hydroperoxide (9.6 mmol; 3 eq.), $CuBr_2$ catalyst as described in the table below and 3.4 g (32 mmol, 10 eq.) of ethylbenzene is stirred at 60° C. for 1 h. In some of the preparations, 0.032 mmol (0.01 eq. relative to TEMPO) of a phase transfer catalyst as shown in the table is added. Reaction and work-up is done as described in example 1. Yield is determined by means of quantitative HPLC.

TABLE

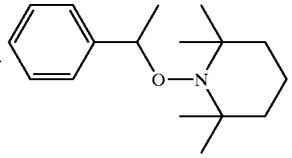

Synthesis of [structure] with and without phase transfer catalyst

| Run | CuBr$_2$ | Phase Transfer Catalyst | Yield |
|---|---|---|---|
| 1 | 0.357 mg | none | 35% |
| 2 | 0.357 mg | 10.3 mg tetrabutylammonium bromide | 73% |
| 3 | 0.357 mg | 14.4 mg trioctyl-methyl ammonium bromide | 78% |
| 4 | 7.15 mg | none | |

Amounts of copper catalyst 0.375 mg are 0.0016 mmol (0.0005 eq.); 7.15 mg are 0.032 mmol (0.01 eq. rel. to TEMPO).

This example shows that the reaction speed may be increased by adding a phase transfer catalyst or by greatly increasing the amount of copper catalyst.

EXAMPLE 13

2,6-Diethyl-2,3,6-trimethyl-1-(1-phenyl-ethoxy)-piperidine (101)

2.4 ml of a solution of 13.4 g of CuCl$_2$ and 4.24 g of LiCl in 153 ml of ethanol are added to a solution of 29.75 g (0.15 mol) of 2,6-diethyl-2,3,6-trimethyl-piperidine-1-oxyl (accessable according to U.S. Pat. No. 4,131,599) in 92 ml (0.75 mol) of ethylbenzene. 28.7 g (0.22 mol) of t-butyl hydroperoxide (70% in water) are then added dropwise to the stirred mixture at 65° C. under argon. The mixture is then stirred at 65–70° C. until the red nitroxide colour disappears (approximately 3 to 4 hours). After cooling to 20° C., a solution of 12 g of Na$_2$S$_2$O$_5$ in 60 ml of water is added. After stirring for a further 60 minutes, the organic phase is separated off, washed with 2×50 ml of 20% Na$_2$CO$_3$ and 2×50 ml of water, dried over MgSO$_4$ and concentrated by evaporation using a rotary evaporator to yield 41.5 g (91%) of the title compound in the form of a colourless oil.

$^1$H-NMR (300 MHz, CDCl$_3$): 7.3–7.2 m (5H), 4.75–4.68 m (1H), 2.13–0.53 m (27H).

EXAMPLE 14

1,3,3-Trimethyl-2-(1-phenyl-ethoxy)-1,2,3,4-tetrahydro-isoquinoline-1-carboxylic acid methyl ester a) 1,3,3-Trimethyl-1,2,3,4-tetrahydro-isoquinoline-1-carboxylic acid methyl ester-2-oxyl 111 ml (0.67 mol) of a 40% peracetic acid in acetic acid are added dropwise over a period of 30 minutes at 10–20° C. to a solution of 78 g (0.334 mol) of 1,3,3-trimethyl-1,2,3,4-tetrahydro-isoquinoline-1-carboxylic acid methyl ester (see *Synthesis* 677 (1997) for preparation) in 300 ml of ethyl acetate. The mixture is stirred for a further 13 hours at 20° C. and then diluted with 650 ml of water. The organic phase is separated off, washed with 2×250 ml of water and then with 2×250 ml of 10% NaHCO$_3$ solution, dried over MgSO$_4$ and concentrated by evaporation using a rotary evaporator. Chromatography of the residue using hexane/ethyl acetate (2:1) on 1600 g of silica gel and subsequent recrystallisation from hexane yields 44.6 g (54%) of 1,3,3-trimethyl-1,2,3,4-tetrahydro-isoquinoline-1-carboxylic acid methyl ester-2-oxyl in the form of orange crystals, m.p. 53–56° C.

For C$_{14}$H$_{18}$NO$_3$ calculated C 67.72%, H 7.31%, N 5.64%; found C 67.46%, H 7.28%, N 5.64%.

b) Analogously to Example 13, 3.14 g (89%) of compound of example (a) are prepared from 2.5 g (0.01 mol) of 1,3,3-trimethyl-1,2,3,4-tetrahydro-isoquinoline-1-carboxylic acid methyl ester-2-oxyl, 20 ml (0.163 mol) of ethylbenzene, 2.25 g (0.017 mol) of t-butyl hydroperoxide (70% in water) and 0.2 ml of the copper(ll) chloride solution described in Example 13. Colourless resin is obtained after chromatography on silica gel using hexane/ethyl acetate (6:1). $^1$H-NMR (300 MHz, CDCl$_3$), mixture of 2 diastereoisomers: 7.33–6.80 m (9H), 4.96–4.69 m (1H), 3.72–0.88 m (17H).

EXAMPLE 15

1-Methyl-1,3,3-triphenyl-2-(1-phenyl-ethoxy)-2,3-dihydro-1.H.-isoindole a) 1-Methyl-1,3,3-triphenyl-2,3-dihydro-1.H.-isoindole 17.3 g (0.05 mol) of 1,1,3-triphenyl-1.H.-isoindole (see *Zh. Org. Khim.* 2449 (1975) for preparation) are slowly added under argon to a stirred solution of 21.9 g (1 mol) of methyllithium in 115 ml of tetrahydrofuran. The mixture is then heated at 70° C. for 5 hours and subsequently stirred at 20° C. for 12 hours. 100 ml of toluene and 80 ml of saturated NH$_4$Cl solution are then added, and the organic phase is separated off, washed with water and concentrated by evaporation using a rotary evaporator. Chromatography of the residue using hexane/ethyl acetate (49:1) on 250 g of silica gel and subsequent recrystallisation from acetonitrile/methanol yields 10.6 9 (58%) of 1-methyl-1,3,3-triphenyl-2,3-dihydro-1.H.-isoindole in the form of colourless crystals, m.p. 106–108° C.

For C$_{27}$H$_{23}$N calculated C 89.71%, H 6.41%, N 3.87%; found C 89.67%, H 6.51%, N 3.80%.

b) 1-Methyl-1,3,3-triphenyl-2,3-dihydro-1.H.-isoindole-2-oxyl 12.3 g (0.05 mol) of m-chloroperbenzoic acid (70%) are added to a solution of 9.05 g (0.025 mol) of 1-methyl-1,3,3-triphenyl-2,3-dihydro-1.H.-isoindole in 60 ml of tetrahydrofuran. The mixture is stirred at room temperature for 3 hours, then diluted with 50 ml of hexane and 50 ml of ethyl acetate, washed three times with 100 ml of 10% NaHCO$_3$ solution and concentrated by evaporation using a rotary evaporator. Chromatography of the residue using toluene on 150 g of silica gel and subsequent recrystallisation from hexane yields 7.7 g (82%) of 1-methyl-1,3,3-triphenyl-2,3-dihydro-1.H.-isoindole-2-oxyl in the form of orange crystals, m.p. 119–124° C.

For C$_{27}$H$_{22}$NO calculated C 86.14%, H 5.89%, N 3.72%; found C 86.18%, H 5.89%, N 3.68%.

c) Analogously to Example 13, 2.2 g (76%) of the title compound are prepared in the form of colourless crystals (pentane), m.p. 124–141° C., from 2.26 g (0.006 mol) of 1-methyl-1,3,3-triphenyl-2,3-dihydro-1.H.-isoindole-2-oxyl, 20 ml (0.163 mol) of ethylbenzene, 2.53 g (0.02 mol) of t-butyl hydroperoxide (70% in water), 0.2 g of tetrabutylammonium bromide and 0.25 ml of the copper (II) chloride solution described in Example 13.

$^1$H-NMR (300 MHz, CDCl$_3$), mixture of 2 diastereoisomers: 7.95–6.66 m (ArH), 4.64–4.51 m (1H), 1.58 s (Me), 1.43 s (Me), 1.12 d, J=9Hz, (Me), 0.86 d, J=9 Hz, (Me).

EXAMPLE 16

1,1,3,3-Tetraphenyl-2-(1-phenyl-ethoxy)-2,3-dihydro-1.H.-isoindole a) 1,1,3,3-Tetraphenyl-2,3-dihydro-1.H.-isoindole-2-oxyl 22 g (0.089 mol) of m-chloroperbenzoic acid (70%) are added to a solution of 9.5 g (0.022 mol) of 1,1,3,3-tetraphenyl-2,3-dihydro-1.H.-isoindole (see *J.Org.Chem.* 461 (1969) for preparation) in 85 ml of tetrahydrofuran. The mixture is stirred at room temperature for 46 hours, then diluted with 50 ml of toluene and 50 ml of ethyl acetate, washed twice with 100 ml of 10% $NaHCO_3$ solution and concentrated by evaporation using a rotary evaporator. The residue is dissolved again in 100 ml of tetrahydrofuran and is oxidised with a further 10 g (0.04 mol) of m-chloroperbenzoic acid over a period of 20 hours. After the addition of 100 ml of toluene, the residue is washed twice with 100 ml of 10% $NaHCO_3$, dried over $MgSO_4$ and concentrated by evaporation. Crystallisation of the residue from toluene/-dichloromethane yields 12.55 g of 1,1,3,3-tetraphenyl-2,3-dihydro-1.H.-isoindole-2-oxyl in the form of orange crystals, m.p. 250–253° C.

For $C_{32}H_{24}NO$ calculated C 87.64%, H 5.52%, N 3.19%; found C 87.46%, H 5.58%, N 3.37%.

b) Analogously to Example 13, 2.39 g (88%) of the title compound 104 are prepared in the form of colourless crystals (hexane), m.p. 166–171° C., from 2.2 g (0.005 mol) of 1,1,3,3-tetraphenyl-2,3-dihydro-1.H.-isoindole-2-oxyl, 20 ml (0.163 mol) of ethylbenzene, 2.1 g (0.016 mol) of t-butyl hydroperoxide (70% in water), 0.2 g of tetrabutylammonium bromide and 0.2 ml of the copper(II) chloride solution described in Example 13.

$^1$H-NMR (300 MHz, $CDCl_3$): 7.75–6.56 m (29H), 4.75–4.68 q, J=9 Hz, (1 H), 1.58 s (Me), 0.97 d, J=9 Hz, (Me).

EXAMPLE 17

Phenyl-(2,2,6,6-tetramethyl-piperidin-1-yloxy)-acetic Acid Methyl Ester 4.2 ml (0.03 mol) of t-butyl hydroperoxide (70% in water) and 0.4 ml of the copper(II) chloride solution described in Example 13 are added to a solution of 3.15 g (0.02 mol) of 2,2,6,6-tetramethyl-piperidine-1-oxyl in 14 ml (0.1 mol) of phenylacetic acid methyl ester. The mixture is then stirred at 60° C. under argon until the red colour of the nitroxide disappears (approximately 5 hours). After cooling to room temperature, a solution of 3 g of $Na_2S_2O_5$ in 25 ml of water is added and the mixture was stirred vigorously for a further 10 minutes. The organic phase is then separated off and the excess phenylacetic acid methyl ester is distilled off at 0.1 mbar. The residue is chromatographed on 100 g of silica gel using hexane/ethyl acetate (20:1) and then recrystallised from hexane to yield 3.65 g (59%) of the title compound in the form of colourless crystals, m.p. 83–86° C.

$^1$H-NMR (300 MHz, $CDCl_3$): 7.45–7.26 m (5H), 5.21 s (1H), 3.65 s (Me), 1.64–1.28 m (6H), 1.23 s (Me), 1.14 s (Me), 1.07 s (Me), 0.72 s (Me).

EXAMPLE 18

2,2-Dimethyl-propionic acid 1-(methoxycarbonyl-phenyl-methoxy)-2,2,6,6-tetramethyl-piperidin-4-yl ester Analogously to Example 17, 4.42 g (54%) of the title compound are obtained in the form of colourless crystals, m.p. 138–141° C., from 5.13 g (0.02 mol) of 2,2-dimethyl-propionic acid 2,2,6,6-tetramethyl-piperidin-4-yl ester-1-oxyl (prepared from pivaloyl chloride and 2,2,6,6-tetramethyl-4-hydroxy-piperidine-1-oxyl in pyridine, m.p. 94–97° C.), 14 ml (0.1 mol) of phenylacetic acid methyl ester, 4.2 ml (0.03 mol) of t-butyl hydroperoxide (70% in water) and 0.4 ml of the copper(II) chloride solution described in Example 13.

$^1$H-NMR (300 MHz, $CDCl_3$): 7.44–7.26 m (5H), 5.19 s (1 H), 5.03–4.93 m (1H), 3.66 s (Me), 1.87–1.43 m (4H), 1.34 s (Me), 1.19 s (Me), 1.17 s (Me), 1.16 s (t-Bu), 0.76 s (Me).

EXAMPLE 19

(4-Acetylaino-2,2,6,6-tetramethyl-piperidin-1-yloxy)-phenyl-acetic acid methyl ester Analogously to Example 17, 21.5 g (59%) of the title compound are obtained in the form of colourless crystals, m.p. 160–161° C., from 21.23 g (0.1 mol) of 4-acetylamino-2,2,6,6-tetramethyl-piperidine-1-oxyl, 70.4 ml (0.5 mol) of phenylacetic acid methyl ester, 20.6 ml (0.15 mol) of t-butyl hydroperoxide (70% in water) and 2 ml of the copper(II) chloride solution described in Example 13.

$^1$H-NMR (300 MHz, $CDCl_3$): 7.44–7.26 m (5H), 5.18 s (1H), 5.11 s (1H), 4.15–4.13 m (1H), 3.66 s (Me), 1.93 s (Me), 1.85–1.26 m (4H), 1.58 s (Me), 1.35 s (Me), 1.18 s (Me), 0.75 s (Me).

EXAMPLE 20

(4-tert-Butyl-2,2-diethyl-6,6-dimethyl-3-oxo-piperazin-1-yloxy)-phenylacetic acid methyl ester Analogously to Example 17, 4.9 g (60%) of the title compound are obtained in the form of colourless crystals, m.p. 85–90° C., from 5.1 g (0.02 mol) of 4-tert-butyl-2,2-diethyl-6,6-dimethyl-3-oxo-piperazine-1-oxyl (see Ger. Offen. DE 199 49 352 A1 for preparation), 14 ml (0.1 mol) of phenylacetic acid methyl ester, 4.2 ml (0.03 mol) of t-butyl hydroperoxide (70% in water) and 0.4 ml of the copper(II) chloride solution described in Example 13.

$^1$H-NMR (300 MHz, $CDCl_3$): 7.42–7.26 m (5H), 5.19–5.18 bs (1H), 3.68 s (Me), 3.11–2.95 m (2H), 1.39 s (t-Bu), 2.25–0.73 m (16 H).

EXAMPLE 21

(4-tert-Butyl -2,2-diethyl-6,6-dimethyl-3-oxo-piperazin-1-yloxy)-phenylacetic acid 2 g (0.0049 mol) of compound of example 20 are added to a solution of 2 g of KOH in 15 ml of methanol and the mixture is stirred at room temperature for 15 hours. It is then concentrated by evaporation using a rotary evaporator and the residue is dissolved in 15 ml of water and acidified with 4 ml of HCl (32%). The resulting precipitate is filtered off with suction and recrystallised from acetonitrile to yield 1.2 g (62%) of the title compound in the form of colourless crystals, m.p. 125–133° C.

$^1$H-NMR (300 MHz, $CDCl_3$): 7.41–7.26 m (5H), 5.19 s (1H), 3.07–2.99 m (2H), 1.43 s (t-Bu), 2.35–0.72 m (16 H).

EXAMPLE 22

Phenyl-(2,2,6,6-tetramethyl-piperidin-1-yloxy)-acetonitrile

Analogously to Example 17, 2.45 g (45%) of the title compound are obtained in the form of colourless crystals, m.p. 33–36° C., from 3.15 g (0.02 mol) of 2,2,6,6-tetramethyl-piperidine-1-oxyl, 12 ml (0.1 mol) of benzyl cyanide, 4.2 ml (0.03 mol) of t-butyl hydroperoxide (70% in water) and 0.4 ml of the copper(II) chloride solution described in Example 13.

$^1$H-NMR (300 MHz, CDCl$_3$): 7.48–7.25 m (5H), 5.55 s (1H), 1.66–1.35 m (6H), 1.45 s (Me), 1.16 s (Me), 1.08 s (Me), 1.00 s (Me).

EXAMPLE 23

Acetic acid 2:phenyl-2-(2,2,6,6-tetramethyl-piperidin-1-yloxy)-ethyl ester 10 g (0.064 mol) of tetramethyl-piperidine-1-oxyl, 52.6 g (0.32 mol) of 2-phenylethyl acetate, 100 mg of copper(I) bromide, 250 mg of tetrabutylammonium bromide and 16 ml of water are placed in a 350 ml sulfonating flask under nitrogen. With stirring, the mixture is heated to 50° C. and then, at 50–55° C., 24.5 g (0.19 mol) of t-butyl hydroperoxide (70% in water) are added dropwise in 30 minutes. The mixture is then stirred at 65–70° C. until the red nitroxide colour disappears (approximately from 8 to 10 hours). After cooling to 20° C., a solution of 10 g of Na$_2$S$_2$O$_5$ in 50 ml of water is added. After stirring for a further 60 minutes, the organic phase is separated off, washed with 2×50 ml of 20% Na$_2$CO$_3$ and 2×50 ml of water and dried over MgSO$_4$, and the excess 2-phenylethyl acetate is distilled off at 80–90° C. under a high vacuum. The solid residue is recrystallised from hexane to yield 8.6 g (42%) of the title compound in the form of white crystals having a melting point of 39–41° C.

EXAMPLE 24

2,2-Dimethylpropionic acid 1-(2-acetoxy-1-phenyl-ethoxy)-2,2,6,6-tetramethyl-piperidin-4-yl ester The title compound is prepared analogously to Example 23. 20.0 g (0.078 mol) of 2,2-dimethyl-propionic acid 2,2,6,6-tetramethyl-piperidin4-yl ester-1-oxyl are reacted with 64 g (0.39 mol) of 2-phenylethyl acetate and 30 g of t-butyl hydroperoxide (70% in water). The crude product is recrystallised from pentane and 17.2 g (53%) of compound 112 are obtained in the form of white crystals having a melting point of 102–103° C.

EXAMPLE 25

Acetic acid 2-(4-hydroxy-2,2,6,6-tetramethyl-piperidin-1-yloxy)-2-phenylethyl ester The title compound is prepared analogously to Example 23. 10.0 g (0.058 mol) of 4-hydroxy-2,2,6,6-tetramethyl-piperidine-1-oxyl are reacted with 47.6 g (0.29 mol) of 2-phenylethyl acetate and 16 g of t-butyl hydroperoxide (70% in water). The crude product is recrystallised from pentane and 8.4 g (43%) of the title compound are obtained in the form of white crystals having a melting point of 68–69° C.

EXAMPLE 26

Acetic acid 2-(4-tert-butyl-2,2-diethyl-6,6-dimethyl-3-oxo-piperazin-1-yloxy)-2-phenylethyl ester The title compound is prepared analogously to Example 23. 10.2 g (0.04 mol) of 4-tert-butyl-2,2-diethyl-6,6-dimethyl-3-oxo-piperazine-1-oxyl are reacted with 32.1 g (0.19 mol) of 2-phenylethyl acetate and 21 g of t-butyl hydroperoxide (70% in water). After working up, 14.0 g (85%) of the crude compound 114 are obtained in the form of a yellow oil.

$^1$H-NMR (300 MHz, CDCl$_3$) mixture of diastereoisomers: 7.3–7.1 m (5H Ar), 4.8–4.7 m (1H), 4.6–4.1 m (2H), 3.1–2.8 m (2H), 1.38 s (t-Bu), 2.1–0.5 m (28 H).

EXAMPLE 27

Acetic acid 2-(4-acetylamino-2,2,6,6-tetramethyl-piperidin-1-yloxy)-2-phenylethyl ester The title compound is prepared analogously to Example 23. 91.4 g (0.43 mol) of 4-acetylamino-2,2,6,6-tetramethyl-piperidine-1-oxyl are reacted with 261 g (1.6 mol) of 2-phenylethyl acetate and 166 g of t-butyl hydroperoxide (70% in water). The crude product is dissolved in 500 ml of diethyl ether and then precipitated in 2.5 litres of hexane to yield 119.2 g (74%) of the title compound in the form of white crystals having a melting point of 109–110° C.

What is claimed is:

1. Process for the preparation of an amine ether of the formula A

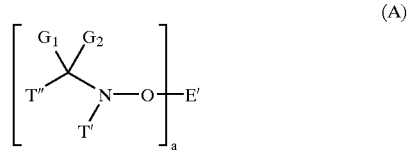

(A)

wherein a is 1 or 2;

when a is 1, E' is E when a is 2, E' is L;

E is a radical of formula (VII)

(VII)

wherein

X is phenyl, naphthyl or biphenyl, which is substituted by 1, 2, 3 or 4 D and optionally further substituted by NO$_2$, halogen, amino, hydroxy, cyano, carboxy, C$_1$–C$_4$alkoxy, C$_1$–C$_4$alkylthio, C$_1$–C$_4$alkylamino or di(C$_1$–C$_4$alkyl)amino;

D is a group

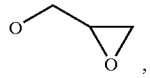

a group C(O)—G$_{13}$ or a group C(O)—G$_9$—C(O)—G$_{13}$—;

G$_1$ and G$_2$, independently of each other, are hydrogen, halogen, NO$_2$, cyano, —CONR$_5$R$_6$, —(R$_9$)COOR$_4$, —C(O)—R$_7$, —OR$_8$, —SR$_8$, —NHR$_8$, —N(R$_{18}$)$_2$, carbamoyl, di(C$_1$–C$_{18}$alkyl)carbamoyl, —C(=NR$_5$) (NHR$_6$), C$_1$–C$_{18}$alkyl; C$_3$–C$_{18}$alkenyl; C$_3$–C$_{18}$alkinyl, C$_7$–C$_9$phenylalkyl, C$_3$–C$_{12}$cycloalkyl or C$_2$–C$_{12}$heterocycloalkyl; C$_1$–C$_{18}$alkyl or C$_3$–C$_{18}$alkenyl or C$_3$–C$_{18}$alkinyl or C$_7$–C$_9$phenylalkyl, C$_3$–C$_{12}$cycloalkyl or C$_2$–C$_{12}$heterocycloalkyl substituted by OH, halogen, $NO_2$, amino, cyano, carboxy, $COOR_{21}$, $C(O)—R22$, $—C_1—C_4$alkoxy, $C_1—C_4$alkylthio, $C_1—C_4$alkylamino or di($C_1—C_4$alkyl)amino or a group $—O—C(O)—R_7$; $C_2—C_{18}$alkyl which is interrupted by at least one O atom and/or $NR_5$ group; or are $C_6—C_{10}$aryl; or phenyl or naphthyl which are substituted by $C_1—C_4$alkyl, $C_1—C_4$alkoxy, $C_1—C_4$alkylthio, halogen, cyano, hydroxy, carboxy, $COOR_{21}$, $C(O)—R_{22}$, $C_1—C_4$alkylamino or di($C_1—C_4$alkyl)amino; or $G_1$ and $G_2$ together with the linking carbon atom form a $C_3—C_{12}$cycloalkyl radical;

$G_5$ and $G_6$ are independently of each other H or $CH_3$;

$G_9$ is $C_1—C_{12}$alkylene or a direct bond;

$G_{13}$ is $C_1—C_{18}$alkyl;

L is alkylene of 1 to 18 carbon atoms, cycloalkylene of 5 to 8 carbon atoms, cycloalkenylene of 5 to 8 carbon atoms, alkenylene of 3 to 18 carbon atoms, alkylene of 1 to 12 carbon atoms substituted by phenyl or by phenyl substituted by alkyl of 1 to 4 carbon atoms; or is alkylene of 4 to 18 carbon atoms interrupted by COO and/or phenylene;

T″ and T′ together form a divalent organic linking group completing, together with the hindered amine nitrogen atom and the quaternary carbon atom substituted by $G_1$ and $G_2$, an optionally substituted five- or six-membered ring structure; and $R_4$ is hydrogen, $C_1—C_{18}$alkyl, phenyl, an alkali metal cation or a tetraalkylammonium cation;

$R_5$ and $R_6$ are hydrogen, $C_1—C_{18}$alkyl, $C_2—C_{18}$alkyl which is substituted by hydroxy or, taken together, form a $C_2—C_{12}$alkylene bridge or a $C_2—C_{12}$-alkylene bridge interrupted by O or/and $NR_{18}$;

$R_7$ is hydrogen, $C_1—C_{18}$alkyl or $C_6—C_{10}$aryl;

$R_8$ is hydrogen, $C_1—C_{18}$alkyl or $C_2—C_{18}$hydroxyalkyl;

$R_9$ is $C_1—C_{12}$alkylene or a direct bond;

$R_{18}$ is $C_1—C_{18}$alkyl or phenyl, which are unsubstituted or substituted by halogen, OH, $COOR_{21}$ or $C(O)—R_{22}$;

$R_{21}$ is hydrogen, a alkali metal atom or $C_1—C_{18}$alkyl; and $R_{22}$ is $C_1—C_{18}$alkyl;

which process comprises reacting a N-oxyl amine of formula B

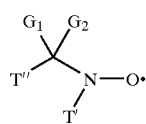 (B)

with a compound of formula IV or V

E—H (IV)

H—L—H (V)

in the presence of an organic hydroperoxide and a catalytic amount of copper or a copper compound.

2. Process for the preparation of an amine ether of the formula A according to claim 1

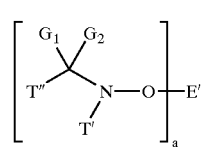 (A)

wherein a is 1 or 2;

when a is 1, E′ is E when a is 2, E′ is L;

E is a radical of formula (VII)

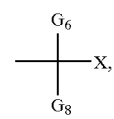 (VII)

wherein

X is phenyl, naphthyl or biphenyl, which are substituted by 1, 2, 3 or 4 D and optionally further substituted by $NO_2$, halogen, amino, hydroxy, cyano, carboxy, $C_1—C_4$alkoxy, $C_1—C_4$alkylthio, $C_1—C_4$alkylamino or di($C_1—C_4$alkyl)amino;

D is a group

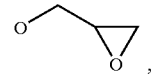

a group $C(O)—G_{13}$ or a group $C(O)—G_9—C(O)—G_{13}$—;

$G_1$ and $G_2$, independently of each other, are hydrogen, halogen, $NO_2$, cyano, $—CONR_5R_6$, $—(R_9)COOR_4$, $—C(O)—R_7$, $—OR_8$, $—SR_8$, $—NHR_8$, $—N(R_{18})_2$, carbamoyl, di($C_1—C_{18}$alkyl)carbamoyl, $—C(=NR_5)(NHR_6)$, $C_1—C18$alkyl; $C_3—C_{18}$alkenyl; $C_3—C_{18}$alkinyl, $C_7—C_9$phenylalkyl, $C_3—C_{12}$cycloalkyl or $C_2—C_{12}$heterocycloalkyl; $C_1—C_{18}$alkyl or $C_3—C_{18}$alkenyl or $C_3—C_{18}$alkinyl or $C_7—C_9$phenylalkyl, $C_3—C_{12}$cycloalkyl or $C_2—C_{12}$heterocycloalkyl substituted by OH, halogen, $NO_2$, amino, cyano, carboxy, $COOR_{21}$, $C(O)—R_{22}$, $C_1—C_4$alkoxy, $C_1—C_4$alkylthio, $C_1—C_4$alkylamino or di($C_1—C_4$alkyl)amino or a group $—O—C(O)—R_7$; $C_2—C_{18}$alkyl which is interrupted by at least one O atom and/or $NR_5$ group; or are $C_6—C_{10}$aryl; or phenyl or naphthyl which are substituted by $C_1—C_4$alkyl, $C_1—C_4$alkoxy, $C_1—C_4$alkylthio, halogen, cyano, hydroxy, carboxy, $COOR_{21}$, $C(O)—R_{22}$, $—C_1—C_4$alkylamino or di($C_1—C_4$alkyl)amino; or $G_1$ and $G_2$ together with the linking carbon atom form a $C_3—C_{12}$cycloalkyl radical;

$G_6$ and $G_6$ are independently of each other H or $CH_3$;

$G_9$ is $C_1—C_{12}$alkylene or a direct bond;

$G_{13}$ is $C_1—C_{18}$alkyl;

L is alkylene of 1 to 18 carbon atoms, cycloalkylene of 5 to 8 carbon atoms, cycloalkenylene of 5 to 8 carbon atoms, alkenylene of 3 to 18 carbon atoms, alkylene of 1 to 12 carbon atoms substituted by phenyl or by phenyl substituted by alkyl of 1 to 4 carbon atoms;

T″ and T′ together form a divalent organic linking group completing, together with the hindered amine nitrogen atom and the quaternary carbon atom substituted by $G_1$ and $G_2$, an optionally substituted five- or six-membered ring structure; and $R_4$ is hydrogen, $C_1$–$C_{18}$alkyl, phenyl, an alkali metal cation or a tetraalkylammonium cation;

$R_5$ and $R_6$ are hydrogen, $C_1$–$C_{18}$alkyl, $C_2$–$C_{18}$alkyl which is substituted by hydroxy or, taken together, form a $C_2$–$C_{12}$alkylene bridge or a $C_2$–$C_{12}$-alkylene bridge interrupted by O or/and $NR_{18}$;

$R_7$ is hydrogen, $C_1$–$C_{18}$alkyl or $C_6$–$C_{10}$aryl;

$R_8$ is hydrogen, $C_1$–$C_{18}$alkyl or $C_2$–$C_{18}$hydroxyalkyl;

$R_9$ is $C_1$–$C_{12}$alkylene or a direct bond;

$R_{18}$ is $C_1$–$C_{18}$alkyl or phenyl, which are unsubstituted or substituted by halogen, OH, $COOR_{21}$ or C(O)—$R_{22}$;

$R_{21}$ is hydrogen, a alkali metal atom or $C_1$–$C_{18}$alkyl; and $R_{22}$ is $C_1$–$C_{18}$alkyl;

which process comprises reacting a N-oxyl amine of formula B

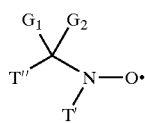

(B)

with a hydrocarbon of formula IV or V

 E—H (IV)

 H—L—H (V)

in the presence of an organic hydroperoxide and a catalytic amount of copper or a copper compound.

3. Process according to claim 1, wherein the compound of formula A corresponds to formula I or II

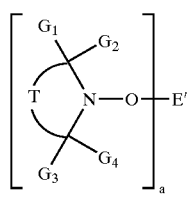

(I)

wherein $G_1$, $G_2$, $G_3$ and $G_4$ independently of each other are $C_1$–$C_{18}$alkyl; $C_3$–$C_{18}$alkenyl; $C_3$–$C_{18}$alkinyl; $C_1$–$C_{18}$alkyl or $C_3$–$C_{18}$alkenyl or $C_3$–$C_{18}$alkinyl substituted by OH, halogen or a group —O—C(O)—$R_5$; $C_2$–$C_{18}$alkyl which is interrupted by at least one O atom and/or $NR_5$ group; or are $C_3$–$C_{12}$cycloalkyl; or $C_6$–$C_{10}$aryl; or $G_1$ and $G_2$ and/or $G_3$ and $G_4$ together with the linking carbon atom form a $C_3$–$C_{12}$cycloalkyl radical;

a is 1 or 2;

when a is 1, halogen; $C_7$–$C_{15}$ aralkyl or $C_7$–$C_{15}$ aralkyl substituted by $C_1$–$C_4$ alkyl or E' is a radical of formula (VII)

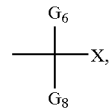

(VII)

wherein

X is phenyl, naphthyl or biphenyl, which are substituted by 1, 2, 3 or 4 D and optionally further substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino;

D is a group

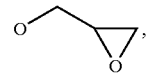

a group C(O)—$G_{13}$ or a group C(O)—$G_9$—C(O)—$G_{13}$;

when a is 2, E' is L;

$G_5$ and $G_6$ are independently of each other H or $CH_3$;

$G_9$ is $C_1$–$C_{12}$alkylene or a direct bond;

$G_{13}$ is $C_1$–$C_{18}$alkyl;

L is alkylene of 1 to 18 carbon atoms, cycloalkylene of 5 to 8 carbon atoms, cycloalkenylene of 5 to 8 carbon atoms, alkenylene of 3 to 18 carbon atoms, alkylene of 1 to 12 carbon atoms substituted by phenyl or by phenyl substituted by alkyl of 1 to 4 carbon atoms;

T is a divalent organic radical required to complete formula 1 to form, together with the hindered amine nitrogen atom and the two quaternary carbon atoms substituted by $G_1$ and $G_2$ or $G_3$ and $G_4$, a five- or six-membered ring structure;

which process comprises reacting a N-oxyl hindered amine of formula III

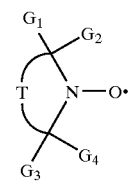

(III)

with a compound formula IV or V

 E—H (IV)

 H—L—H (V)

in the presence of an organic hydroperoxide and a catalytic amount of copper or a copper compound.

4. Process according to claim 1, wherein the organic hydroperoxide is a peroxoalcohol containing 3–18 carbon atoms.

5. Process according to claim 1, wherein 1 to 100 moles of the compound of formula IV or V, 1 to 20 moles of organic hydroperoxide, and 0.001 mmoles to 0.5 moles of copper catalyst are used per mole of N-oxyl compound of formula B.

6. Process according to claim 1, wherein the compound of formula IV or V is used in excess and serves both as reactant and as solvent for the reaction and/or wherein a further inert organic or inorganic solvent is used.

7. Process according to any of claim 1 wherein the reaction is carried out in the presence of a phase transfer catalyst.

8. Process according to claim 1, wherein the catalyst is formed from an inorganic Cu(I) or Cu(II) compound dissolved in a suitable solvent.

9. Process according to claim 3, wherein in the formulae I and III T is an organic linking group containing 2–500 carbon atoms and 0–200 hetero atoms selected from oxygen, phosphorus, sulfur, silicon, halogen and nitrogen as tertiary nitrogen, and forming, together with the carbon atoms it is directly connected to and the nitrogen atom, an optionally substituted, 5-, 6 or 7-membered cyclic ring structure.

10. Process according to claim 1 wherein the product formed corresponds to one of the formulae

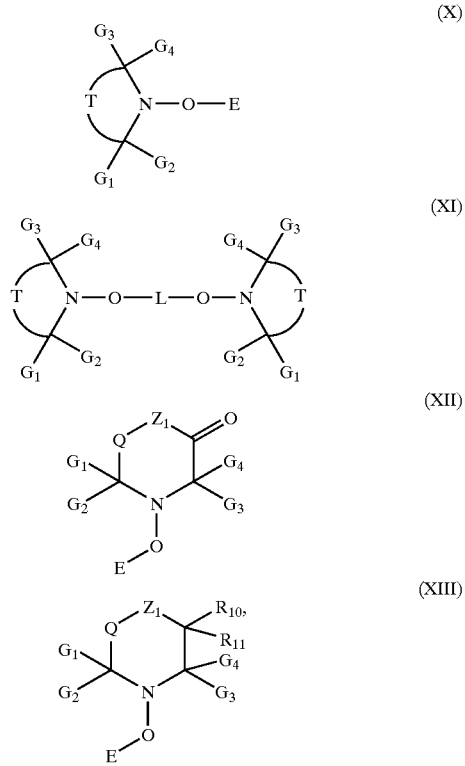

wherein
$G_1$, $G_2$, $G_3$ and $G_4$ independently of each other are $C_1$–$C_{18}$alkyl; $C_3$–$C_{18}$alkenyl; $C_3$–$C_{18}$alkinyl; $C_1$–$C_{18}$alkyl or $C_3$–$C_{18}$alkenyl or $C_3$–$C_{18}$alkinyl substituted by OH, halogen or a group —O—C(O)—$R_5$; $C_2$–$C_{18}$alkyl which is interrupted by O; $C_5$–$C_{12}$cycloalkyl; or phenyl; or $G_1$ and $G_2$ and/or $G_3$ and $G_4$ together with the linking carbon atom form a $C_5$–$C_{12}$cycloalkyl radical;

$Z_1$ is O or $NR_8$;

$R_8$ is hydrogen, OH, $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by one or more OH, halogen or a group —O—C(O)—$R_5$, $C_2$–$C_{18}$alkyl which is interrupted by at least one O atom and/or $NR_5$ group, $C_3$–$C_{12}$cycloalkyl or $C_6$–$C_{10}$aryl, $C_7$–$C_9$phenylalkyl, $C_5$–$C_{10}$heteroaryl, —C(O)—$C_1$–$C_{18}$alkyl, —O—$C_1$–$C_{18}$alkyl or —COO$C_1$–$C_{18}$alkyl;

Q is a direct bond or a divalent radical $CR_9R_{10}$, $CR_9R_{10}$—$CR_{11}R_{12}$, $CR_9R_{10}CR_{11}R_{12}CR_{13}R_{14}$, C(O) or $CR_9R_{10}C(O)$;

$R_9$, $R_{10}$, $R_{11}$, $R_{12}$, $R_{13}$ and $R_{14}$ are independently hydrogen, phenyl, or $C_1$–$C_{18}$alkyl;

T is $CH_2$—$C(R_{24})(R_{25})$—$CH_2$, wherein $R_{24}$ and $R_{25}$ together are =O or independently are H, OH or an organic residue, characterized in that the linking group T in total contains 2–500 carbon atoms and optionally 1–200 hetero atoms selected from, oxygen, phosphorus, sulfur, silicon, halogen and tertiary nitrogen.

11. Process according to claim 3 for the preparation of a compound of formula (I), wherein in the formulae (I)

$G_1$, $G_2$, $G_3$ and $G_4$, independently of each other, are methyl, ethyl, phenyl or $COOR_4$;

$R_4$ is hydrogen or $C_1$–$C_8$alkyl;

L is a carbon centered radical formed from propane, butane, pentane, 2,2-dimethyl-propane, xylene; and T is phenylene or an organic linking group of the formula

$E_2$ is —CO— or —$(CH_2)_b$—, while b is 0, 1 or 2;

$E_1$ is a carbon atom carrying the two residues $R_{24}$ and $R_{25}$, or is >N—$R_{25}$, or is oxygen, and $R_{24}$ and $R_{25}$ are hydrogen or an organic residue, characterized in that the linking group T in total contains 2–500 carbon atoms and forms, together with the carbon atoms it is directly connected to it and the nitrogen atom, a substituted, 5-, 6 or 7-membered cyclic ring structure, or wherein $R_{24}$ and $R_{25}$ together are =O or wherein $R_{24}$ is hydrogen and $R_{25}$ is hydrogen or hydroxy;

or $E_1$ and $E_2$ together are 1,2-phenylene.

12. Process according to claim 1, wherein the organic hydroperoxide is tert-butyl-hydroperoxide.

* * * * *